United States Patent
Connolly et al.

(10) Patent No.: US 9,975,881 B2
(45) Date of Patent: *May 22, 2018

(54) COMPOUND

(71) Applicant: ASTRAZENECA AB, Sodertalje (SE)

(72) Inventors: Stephen Connolly, Mölndal (SE);
Mark Richard Ebden, Cheshire (GB);
Iain Alastair Stewart Walters,
Cheshire (GB); Thomas Langer,
Cheshire (GB); Alan Robert Steven,
Cheshire (GB); Craig Robert Stewart,
Cheshire (GB); **Paula Margaret
Tomlin, Cheshire (GB); Andrew John
Williams**, Cheshire (GB)

(73) Assignee: ASTRAZENECA AB, Sodertalje (SE)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/980,754

(22) Filed: Dec. 28, 2015

(65) Prior Publication Data

US 2016/0108023 A1 Apr. 21, 2016

Related U.S. Application Data

(63) Continuation of application No. 14/253,288, filed on Apr. 15, 2014, now Pat. No. 9,221,782, which is a continuation of application No. 13/546,444, filed on Jul. 11, 2012, now Pat. No. 8,735,413.

(60) Provisional application No. 61/506,737, filed on Jul. 12, 2011.

(51) Int. Cl.
| | |
|---|---|
| *A61K 31/506* | (2006.01) |
| *C07D 403/12* | (2006.01) |
| *C07C 69/92* | (2006.01) |
| *C07D 205/04* | (2006.01) |
| *C07D 317/20* | (2006.01) |
| *C07D 317/24* | (2006.01) |
| *C07D 239/56* | (2006.01) |
| *C07C 65/21* | (2006.01) |
| *C07D 317/18* | (2006.01) |
| *C07D 317/26* | (2006.01) |
| *C07D 307/12* | (2006.01) |
| *C07C 69/78* | (2006.01) |

(52) U.S. Cl.
CPC .......... *C07D 403/12* (2013.01); *A61K 31/506* (2013.01); *C07C 65/21* (2013.01); *C07C 69/92* (2013.01); *C07D 205/04* (2013.01); *C07D 239/56* (2013.01); *C07D 317/18* (2013.01); *C07D 317/20* (2013.01); *C07D 317/24* (2013.01); *C07D 317/26* (2013.01); *C07C 69/78* (2013.01); *C07D 307/12* (2013.01)

(58) Field of Classification Search
CPC .................................................. C07D 403/12
See application file for complete search history.

(56) References Cited

U.S. PATENT DOCUMENTS

| | | | |
|---|---|---|---|
| 3,457,278 A | 7/1969 | Zimmermann | |
| 6,201,027 B1* | 3/2001 | Aho ...................... | C07C 317/24 514/675 |
| 7,838,675 B2 | 11/2010 | Cheshire et al. | |
| 8,269,002 B2 | 9/2012 | Cheshire et al. | |
| 8,410,123 B2 | 4/2013 | Cheshire et al. | |
| 2006/0025432 A1 | 2/2006 | Ebden et al. | |
| 2008/0096860 A1 | 4/2008 | Cheshire et al. | |
| 2010/0016275 A1 | 1/2010 | Meghani et al. | |
| 2010/0063079 A1 | 3/2010 | Ebden et al. | |
| 2011/0124919 A1 | 5/2011 | Ernst et al. | |
| 2012/0015927 A1 | 1/2012 | Gullberg et al. | |
| 2012/0157431 A1 | 6/2012 | Cheshire et al. | |

(Continued)

FOREIGN PATENT DOCUMENTS

| | | |
|---|---|---|
| WO | 2004/011443 A1 | 2/2004 |
| WO | 2006/024823 A1 | 3/2006 |

(Continued)

OTHER PUBLICATIONS

J. Luo et al., 36 Cell, 823-837 (2009).*
T. Soussi 60 Cancer Research, 1777-1788 (2000).*
P. Lissoni et al, 7 Cancer Research, 397-401 (2009).*
National Cancer Institute (http://www.cancer.gov/) (Downloaded May 29, 2014).*
F. Bunz, Principles of Cancer Genetics 1-47, 1 (2008).*
P.K. Kuppen et al., 115 Histochemistry and Cell Biology, 67-72 (2001).*
D'Ambrosio et al., 273 Journal of Immunological Methods 3-13 (2003).*
P.J. Koelink et al., 133 Pharmacology & Therapeutics, 1-18 (2012).*
E. R. Sutherland et al., 350 The New England Journal of Medicine, 2689-2697 (2004).*

(Continued)

*Primary Examiner* — Alexander R Pagano
(74) *Attorney, Agent, or Firm* — Daniel Kopp

(57) ABSTRACT

There is provided a compound which is (a) a pyrimidine sulfonamide of formula (I) or (b) a pharmaceutically acceptable salt thereof, crystalline forms of the compound, processes for obtaining the compound, pharmaceutical intermediates used in the manufacture of the compound, and pharmaceutical compositions containing the compound.

(I)

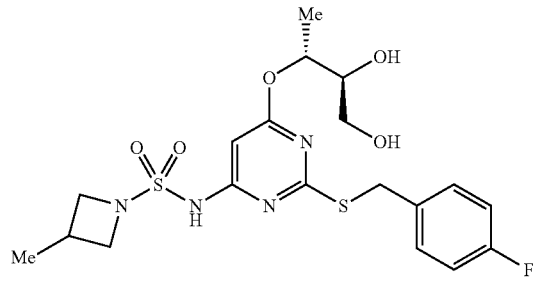

The compound is useful in the treatment of a disease/condition in which modulation of chemokine receptor activity is beneficial.

2 Claims, 2 Drawing Sheets

(56) References Cited

U.S. PATENT DOCUMENTS

| | | |
|---|---|---|
| 2013/0012490 A1 | 1/2013 | Cheshire et al. |
| 2013/0203991 A1 | 8/2013 | Cheshire et al. |

FOREIGN PATENT DOCUMENTS

| | | |
|---|---|---|
| WO | 2010/007427 A1 | 1/2010 |
| WO | 2012/007748 A1 | 1/2012 |

OTHER PUBLICATIONS

S. Judge et al., 111 Pharmacology & Therapeutics, 224-259 (2006).*
V. Brinkmann et al., 9 Nature Reviews | Drug Discovery, 883-897 (2010).*
Z. Wang et al., 19 Drug Discovery Today, 145-150 (2014).*
U.K. Marelli et al., 3 Frontiers in Oncology, 1-12 (2013).*
T.M. Cunha et al., 154 British Journal of Pharmacology, 460-470 (2008).*
D.R. Nagarkar et al., 183 The Journal of Immunology, 6698-6707 (2009).*
J. Belperio et al, 110 The Journal of Clinical Investigation, 1703-1716 (2002).*
R.D. Sue et al., 172 Journal of Immunology, 3860-3868 (2004).*
Abushanab et al., "Practical Enantiospecific Syntheses of (+1) Erythro-9-(2-Hydroxy-3R-Nonyl) Adenine," Tetrahedron Letters, 25: 3841-3844 (1984).
Abushanab et al., "The Chemistry of L-Ascorbic and D-Isoascorbic Acids. 1. The Preparation of Chiral Butanetriols and Hetrols," Journal of Organic Chemistry, 53: 2598-2602 (1988).
Austin et al., "The binding of drugs to hepatocytes and its relationship to physicochemical properties," Drug Metabolism and Disposition, 33: 419-425 (2005).
Braun et al., "Non-Chelate-Controlled Addition of 1-Brono-1lithio-1-alkenes to 0-Protected Lactaldehydes and 3-Alkoxybutyraldehydes," Liebigs Annalen, 1: 29-40 (1995).
International Search Report issued in PCT/GB2012/051620 dated Oct. 18, 2012 (6 pages).
Mulzer et al., "Synthesis of (2R,3S)-1,2,3-Butanetriol Derivatives from (R)-2,3-0-Isopropylideneglyceraldehyde and of the (2S,3R)-Enantiomers from D-Glucose. Application to the Synthesis of Enantiomerically Pure Muscarine," Liebigs Ann. Chem., 1: 7-14 (1987).
Obach et al., "The prediction of human pharmacokinetic parameters from preclinical and in vitro metabolism data," the Journal of Pharmacology and Experimental Therapeutics, 283: 46-58 (1997).
Riley et al., "A unified model for predicting human hepatic, metabolic clearance from in vitro intrinsic clearance data in hepatocytes and microsomes," Drug Metabolism and Disposition, 33: 1304-1311 (2005).
Rychnovsky et al., "Relative and Absolute Configuration of Filipin III," Angewandte Chemie International Edition, 34: 1227-1230 (1995).
Wang et al., "Total synthesis oftrifluoromethylated analogs ofmacrosphelide A," Tetrahedron, 63: 12671-12680 (2007).

* cited by examiner

COMPOUND

This application claims the benefit under 35 U.S.C. § 119(e) of Application No. 61/506,737 (US) filed on 12 Jul. 2011.

FIELD OF THE INVENTION

The present invention relates to certain heterocyclic compounds, processes and intermediates used in their preparation, pharmaceutical compositions containing them and their use in therapy.

BACKGROUND OF THE INVENTION

Chemokines play an important role in immune and inflammatory responses in various diseases and disorders, including asthma and allergic diseases, as well as autoimmune pathologies such as rheumatoid arthritis and atherosclerosis. These small secreted molecules are a growing superfamily of 8-14 kDa proteins characterised by a conserved cysteine motif. At the present time, the chemokine superfamily comprises three groups exhibiting characteristic structural motifs, the C—X—C, C—C and C—$X_3$—C families. The C—X—C and C—C families have sequence similarity and are distinguished from one another on the basis of a single amino acid insertion between the NH-proximal pair of cysteine residues. The C—$X_3$—C family is distinguished from the other two families on the basis of having a triple amino acid insertion between the NH-proximal pair of cysteine residues.

The C—X—C chemokines include several potent chemoattractants and activators of neutrophils such as interleukin-8 (IL-8) and neutrophil-activating peptide 2 (NAP-2).

The C—C chemokines include potent chemoattractants of monocytes and lymphocytes but not neutrophils. Examples include human monocyte chemotactic proteins 1-3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

The C—$X_3$—C chemokine (also known as fractalkine) is a potent chemoattractant and activator of microglia in the central nervous system (CNS) as well as of monocytes, T cells, NK cells and mast cells.

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family. These receptors represent good targets for drug development since agents which modulate these receptors would be useful in the treatment of disorders and diseases such as those mentioned above.

PCT patent applications WO 2004/011443, WO 2006/024823 and WO 2010/007427 disclose pyrimidinyl sulphonamide derivatives for use as modulators of chemokine receptors.

DESCRIPTION OF THE INVENTION

The present invention now provides the compound which is (a) a pyrimidine sulphonamide of formula (I) or (b) a pharmaceutically acceptable salt thereof.

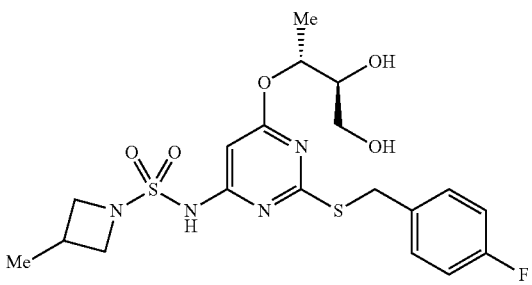 [SMILES: CC1CN(S(=O)(=O)Nc2cc(O[C@H](C)[C@@H](O)CO)nc(SCc3ccc(F)cc3)n2)C1]

(I)

A representative compound of the invention demonstrates an unexpectedly long half-life in dog. A long half-life in pre-clinical species (such as the dog) suggests that a long half-life in human is attainable (Obach et al. (1997), *J. Pharmacol. Exp. Ther.*, 283: 46-58). A half life in human in excess of 12 hours is commensurate with once a day dosing.

In addition, in order to antagonize the target receptor in humans and therefore produce the desired biological effect, a compound should be present in the plasma in sufficient concentration to inhibit the receptor function, and this concentration must be maintained for a sufficient period to continue receptor inhibition between dosing intervals. Thus a compound should exhibit a combination of both high potency and long half life. A representative compound of the invention demonstrates the combination of high potency and long measured half life in dog.

The minimum concentration needed to drive required effect is the Cmin and the maximum concentration reached in the plasma to maintain Cmin at the end of the dosing period (e.g. 24 h for once-a-day) is the Cmax. Hence a small Cmax/Cmin ratio (driven by a long half-life) is beneficial, because high Cmax levels are more likely to cause unwanted effects. The compounds of invention are predicted to have a small Cmax/Cmin ratio.

In a further aspect the compounds of the invention are compounds of formula (I) not in salt-form.

Within the present invention it is to be understood that the compounds of the invention may exhibit the phenomenon of tautomerism and that the formulae within this specification can represent only one of the possible tautomeric forms. It is to be understood that the invention encompasses any tautomeric form and mixtures thereof and is not to be limited merely to any one tautomeric form utilised within the formulae.

A pharmaceutically acceptable salt of compounds of the invention may include a salt prepared from a pharmaceutically acceptable non-toxic base, such as an inorganic or organic base. A salt derived from an inorganic base may be, for example, an aluminium, calcium, potassium, magnesium, sodium or zinc salt. A salt derived from an organic base may be, for example, a salt of a primary, secondary or tertiary amine.

A pharmaceutically acceptable salt of compounds of the invention may be prepared in situ during the final isolation and purification of a compound, or by separately reacting the as compound with a suitable base and isolating the salt thus formed.

The compounds of the invention may exist as a solvate (such as a hydrate) and the present invention covers all such solvates.

The compounds of the invention may exist as an in-vivo hydrolysable ester of the compound of formula (I).

An in-vivo hydrolysable ester of a compound of the invention containing a hydroxy group is, for example, a pharmaceutically-acceptable ester which is hydrolysed in the human or animal body to produce the parent alcohol.

An in-vivo hydrolysable ester of a compound of the invention containing a hydroxy group includes inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxy-methoxy. A selection of in-vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

The compounds of the invention may exist in crystalline form. Thus, according to a further aspect of the invention, there is provided a substantially crystalline form of the compound of formula (I), or pharmaceutically acceptable salts thereof.

When herein reference is made to compounds of the invention being crystalline, suitably the degree of crystallinity as determined by X-ray powder diffraction data is for example greater than about 60%, such as greater than about 80%, particularly greater than about 90%, more particularly greater than about 95%. In embodiments of the invention, the degree of crystallinity as determined by X-ray powder diffraction data is greater than about 98%, wherein the % crystallinity refers to the % by weight of the total sample mass which is crystalline.

It is stated hereinbefore that the compound of formula (I) may be produced in a crystalline form that is an anhydrate. By this we mean that the crystalline form contains less than 10% of hydrate form(s) (e.g. a monohydrate) of the compound of formula (I).

According to a further aspect of the invention, there is provided a substantially crystalline anhydrate form of the compound of formula (I). In a still further aspect, the compound of formula (I) is not in the form of a salt. In a yet still further aspect, the compound of formula (I) is not in the form of a solvate, i.e. it is an "ansolvate". Hence, the term "anhydrate" encompasses "ansolvate".

According to a further aspect of the invention, there is provided an anhydrate crystalline form of the compound of formula (I) which may be characterised by a differential scanning calorimetry curve, at a heating rate of 10° C. per minute in a closed aluminium cup under a nitrogen atmosphere, exhibiting the following onset temperature of the melting endotherm of about 176° C.

According to yet a further aspect of the invention, there is provided a crystalline form of the compound of formula (I) which may be characterised by an X-ray powder diffraction pattern, measured using a wavelength of X-rays 1.5418 Å, comprising the following characteristic peaks with approximate 2-Theta values (in degrees).

Crystalline Form A of N-(6-((2R,3S)-3,4-Dihydroxybutan-2-yloxy)-2-(4-fluorobenzylthio)pyrimidin-4-yl)-3-methylazetidine-1-sulfonamide (hereinafter 'Form A'): a characteristic differential scanning calorimetry curve, at a heating rate of 10° C. per minute in a closed aluminium cup under a nitrogen atmosphere, exhibiting an onset temperature of the melting endotherm of about 176° C.

In a further aspect Form A has an X-ray powder diffraction pattern, measured using a wavelength of X-rays 1.5418 Å, with characteristic peaks at 2-Theta (in degrees) of 8.5, 9.7, 10.6, 17.1, 19.9, and 21.2.

In a further aspect, Form A has an X-ray powder diffraction pattern, measured using a wavelength of X-rays 1.5418 Å, with characteristic peaks at 2-Theta (in degrees) of 8.5, 9.7, 10.6, 17.1, 19.9, and 21.2.

In another aspect, Form A has an X-ray powder diffraction pattern, measured using a wavelength of X-rays 1.5418 Å, with at least three characteristic peaks at 2-Theta (in degrees) selected from 8.5, 9.7, 10.6, 17.1, 19.9, and 21.2.

In a further aspect, Form A has an X-ray powder diffraction pattern, measured using a wavelength of X-rays 1.5418 Å, with at least two characteristic peaks at 2-Theta (in degrees) selected from 8.5, 9.7, 10.6, 17.1, 19.9, and 21.2.

In a still further aspect, Form A has an X-ray powder diffraction pattern, measured using a wavelength of X-rays 1.5418 Å, with at least one characteristic peak at 2-Theta (in degrees) selected from 8.5, 9.7, 10.6, 17.1, 19.9, and 21.2.

In another aspect, Form A comprises the characteristic X-ray powder diffraction pattern peaks, measured using a wavelength of X-rays 1.5418 Å, as shown in FIG. 1.

In another aspect, Form A comprises the characteristic differential calorimetry curve substantially as shown in FIG. 2.

Figure 1:
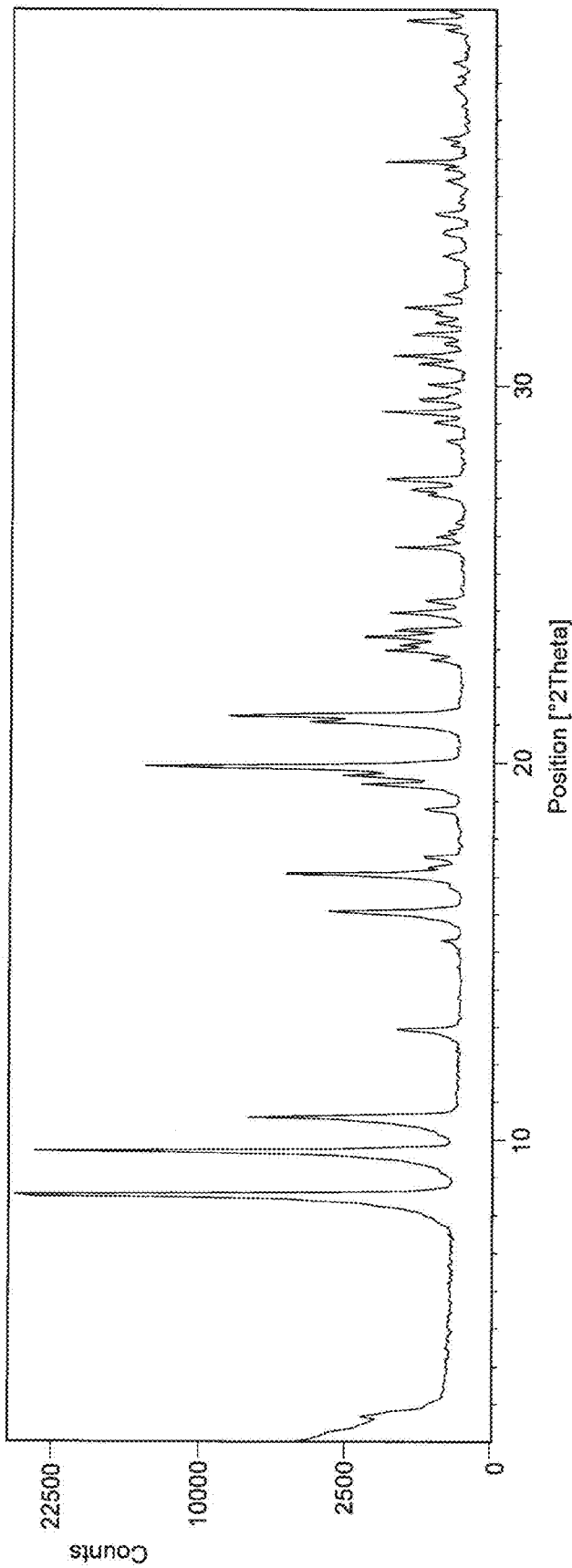
FIG. 1 shows X-ray powder diffractogram of Form A of N-(6-((2R,3S)-3,4-Dihydroxybutan-2-yloxy)-2-(4-fluorobenzylthio)pyrimidin-4-yl)-3-methylazetidine-1-sulfonamide.

Suitably a crystalline modification of a compound according to the invention is substantially free from other crystalline modifications of the compound. Suitably, a described crystalline modification of a compound of formula (I) includes less than, for example, 20%, 15%, 10%, 5%, 3% or particularly, less than 1% by weight of other crystalline forms of that compound.

Crystalline anhydrates of the compound of formula (I) may be prepared as described herein by crystallizing the compound of formula (I) from one or more suitable solvents or mixtures thereof. Anhydrate may be produced by crystallization from a solvent system which is substantially free of water (which may have been dried, and/or may be dried during the crystallization process). Solvent may be dried during the crystallization process, for example by decreasing the water content of a mixture of the compound to be crystallized in a suitable organic solvent/aqueous solvent system (e.g. by increasing the amount of organic solvent that is present and/or removal of water by formation of an azeoptrope, with successive distillations). However, crystalline anhydrates of the compound of formula (I) may also be prepared from water and/or water/alcohol mixtures.

Compounds of the invention that are anhydrates typically contain no more than 2%, particularly 1%, more particularly 0.5% and more particularly 0.2% (w/w) water, whether such water is bound (crystal water or otherwise) or not.

In order to ensure that crystalline forms as described herein are prepared in the absence of other crystalline forms, crystallisations may be carried out by seeding with nuclei and/or seed crystals of the desired crystalline form in the absence of nuclei and/or seed crystals of other crystalline forms.

The skilled person will appreciate that the concentration in solution of the compound that is to be crystallised, and the solvent system that is used, may influence crystallisation temperatures and crystallisation times.

Different crystalline forms may have different solubility in different organic solvents at any given temperature. In this respect, above-mentioned, or other, solvents may be employed as "antisolvents" (i.e. a solvent in which compounds of the invention are poorly soluble, but which is miscible with another solvent, in which compounds of the invention are more soluble), and may thus aid the crystallisation process.

As may be appreciated by the skilled person, the crystalline form that is obtained depends upon both the kinetics and the thermodynamics of the crystallisation process. Under certain thermodynamic conditions (solvent system, temperature, pressure and concentration of the compound of the invention), one crystalline form may be more stable than another (or indeed any other). However, other crystalline forms that may have, in comparison, a relatively low thermodynamic stability, may be kinetically-favoured. Thus, in addition, kinetic factors, such as time, impurity profile, agitation, the presence of seeds, etc. may also influence which forms appear. Thus, the procedures discussed herein may be adapted by the skilled person as appropriate in order to obtain the particular crystalline form of the compound of formula (I).

Compounds of the invention may be dried using standard techniques. It will be appreciated by the skilled person that drying temperature and drying time may affect the solid state properties and/or the solid state form of compounds of the invention. For example, dehydration may occur at low humidity and/or elevated temperatures and/or reduced pressure. Hence, the crystalline anhydrates of compounds of the invention may also be formed by dehydration of a hydrate.

The preparation and characterisation of compounds of the invention may be prepared as described below, by adapting methods known in the art, or by using or adapting the preparative methods described in the Examples. Different crystalline forms of the compounds of the invention may be readily characterised using X-ray powder diffraction (XRPD) methods, for example as described hereinafter. Standard DSC techniques may also be used.

Compounds of the invention may be prepared by following the process presented in Scheme 1 below and in the Examples described herein.

Scheme 1

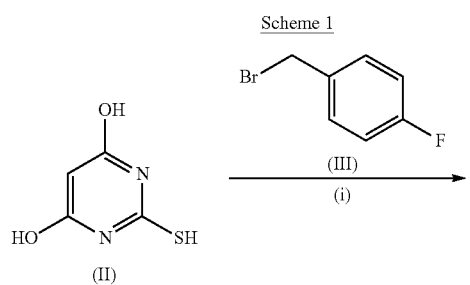

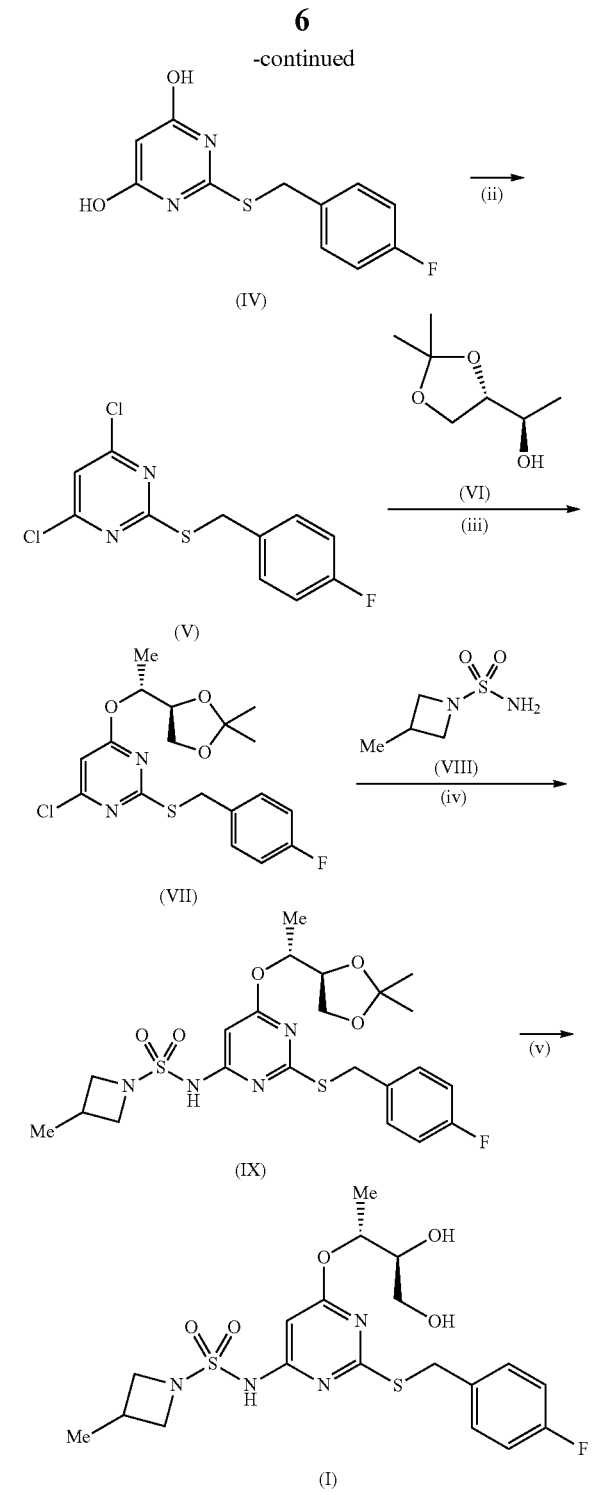

(i) Sodium acetate, water, acetonitrile;
(ii) Phosphorus oxychloride, benzyltriethylammonium chloride, dimethoxyethane;
(iii) Sodium hydride, tetrahydrofuran;
(iv) Cesium carbonate, dicyclohexyl(2',4',6'-triisopropyl-biphenyl-2-yl)phosphine, tris(dibenzylideneacetone)dipalladium(0), dioxane;
(v) Trifluoroacetic acid, dichloromethane.

The compounds of formula (II) and (III) are commercially available or may be synthesised using methods familiar to those skilled in the art.

The compound of formula (VI) may be prepared using a procedure adapted from methods previously described in the literature (see for example Mulzer, J. et al, *Liebigs Ann. Chem.,* 1987, 7-14; Braun, M. et al, *Liebigs Annalen,* 1995, 1, 29-40; Wang, B-L. et al, *Tetrahedron,* 2007, 63(51), 12671-12680). Alternatively the compound of formula (VI) may be prepared by following the processes presented in Scheme 2, Scheme 3 and Scheme 3' below and in the Examples described herein:

Scheme 2

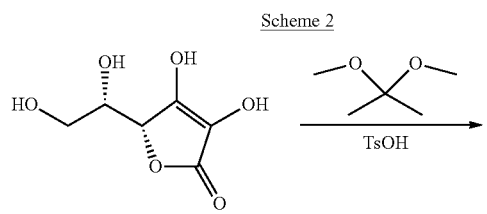

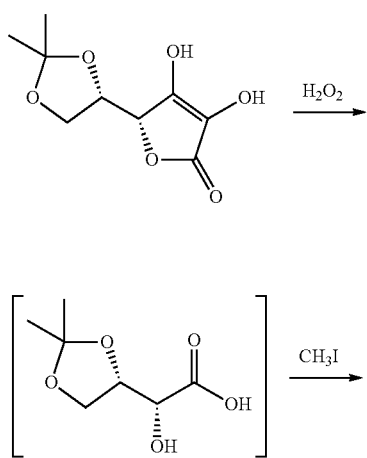

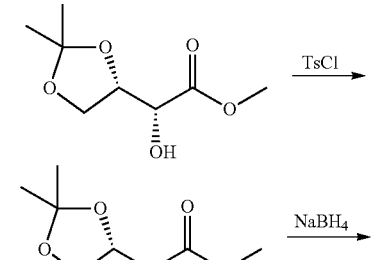

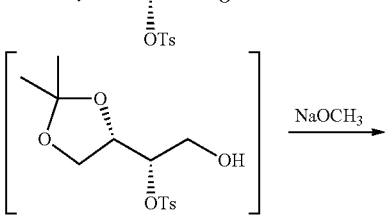

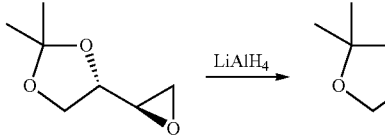

Scheme 3

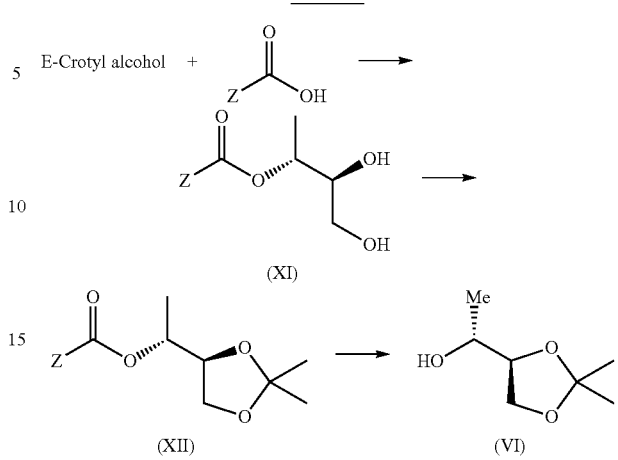

wherein Z is selected from 2,3,4-tri-$C_{1-4}$alkoxyphenyl, 2,4,5-tri-$C_{1-4}$alkoxyphenyl, 2,4,6-tri-$C_{1-4}$alkoxyphenyl, 3,4,5-tri-$C_{1-4}$alkoxyphenyl, 2,3-di-$C_{1-4}$alkoxyphenyl, 2,4-di-$C_{1-4}$alkoxyphenyl, 2,5-di-$C_{1-4}$alkoxyphenyl, 2,6-di-$C_{1-4}$ alkoxyphenyl, 3,4-di-$C_{1-4}$alkoxyphenyl, 3,5-di-$C_{1-4}$ alkoxyphenyl, 3,6-di-$C_{1-4}$alkoxyphenyl, 4-phenylphenyl, 2-$C_{1-4}$alkoxyphenyl, 3-$C_{1-4}$alkoxyphenyl, 4-$C_{1-4}$alkoxyphenyl, 2-nitrophenyl, 3-nitrophenyl, 4-nitrophenyl, 3,5-dinitrophenyl, 1-naphthoic and 2-naphthoic acid. In particular, Z is selected from 3,4,5-tri-$C_{1-4}$alkoxyphenyl, 4-phenylphenyl, 4-$C_{1-4}$ alkoxyphenyl, 2-nitrophenyl, 4-nitrophenyl and 3,5-dinitrophenyl. In one aspect the $C_{1-4}$alkyl group in Z is independently selected from methyl and ethyl and the $C_{1-4}$alkoxy group in Z is independently selected from methoxy and ethoxy. In one aspect Z is 3,4,5-trimethoxyphenyl.

A particular aspect of the process represented in Scheme 3 is shown in Scheme 3'.

Scheme 3'

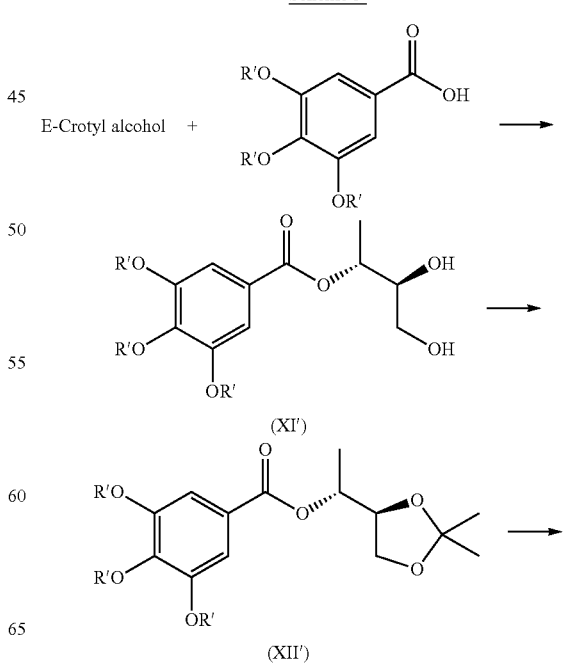

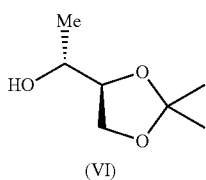

(VI)

wherein R' is $C_{1-4}$alkyl. In particular, R' is independently selected from methyl and ethyl. In another aspect, R' is methyl.

The novel process for the preparation of a compound of the formula (VI) illustrated in scheme 3 has the benefit of a smaller number of steps than previous processes. Hence another aspect of the invention is the preparation of a compound of the formula (VI) from a compound of formula (XII). Another aspect of the invention is the preparation of a compound of formula (VI) from a compound of formula (XI). Another aspect of the invention is the preparation of a compound of the formula (VI) from a compound of formula (XII'). Another aspect of the invention is the preparation of a compound of formula (VI) from a compound of formula (XI').

The compound of formula (VIII) may be prepared by following the process presented in the Examples described herein. In another aspect of the invention there is provided a compound which is (a) an azetidine sulfonamide of formula (VIII), or (b) a salt thereof, hereinafter referred to as "intermediates of the invention".

In Scheme 3, E-crotyl alcohol is conveniently pre-dried using a drying agent. An example of a suitable drying agent is molecular sieves (e.g. molecular sieves 3 Ångstrom). The pre-dried E-crotyl alcohol may be reacted with L-(+)-di-isopropyl tartrate or L-(+)-tert-butyl tartrate in the presence of titanium isopropoxide, in an organic solvent, followed by an organic peroxide such as cumene hydroperoxide before reacting with Z—COOH to give a compound of formula (XI). In one aspect, the combined water content in solvents and reagents in this step does not exceed 0.038 molar equivalents with respect to E-crotyl alcohol.

The compound of formula (XI) may be converted to a compound of formula (XII) by reacting it with dimethoxy-propane in the presence of a catalytic acid, such as para-toluenesulfonic acid, in an organic solvent and subsequently adding a mild aqueous base, such as aqueous potassium bicarbonate solution. Alternatively, a non-aqueous base may be used followed by aqueous work-up.

The compound of formula (XII) may be converted to a compound of the formula (VI) by reacting with a base. A suitable base is, for example, sodium hydroxide.

The compound of the formulae (XI') or salt thereof is novel and forms another aspect of the invention. The compound of the formula (XII') or a salt thereof is novel and forms another aspect of the invention.

In a further aspect of the invention there is provided the use of the intermediates of the invention in the preparation of compounds which modulate chemokine receptor activity. In a still further aspect there is provided the use of the intermediates of the invention in the preparation of a compound of the formula (I) or a pharmaceutically-acceptable salt thereof.

The compounds of the invention have activity as a pharmaceutical, in particular as a modulator of chemokine receptor (especially CXCR2) activity, and may be used in the treatment (therapeutic or prophylactic) of conditions/diseases in human and non-human animals which are exacerbated or caused by excessive or unregulated production of chemokines. Examples of such conditions/diseases include, wherein each condition/disease is taken independently or in any combination thereof:

(1) the respiratory tract—obstructive airways diseases including chronic obstructive pulmonary disease (COPD); asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) bone and joints—rheumatoid arthritis, osteoarthritis seronegative spondyloarthropathies (including ankylosing spondylitis, psoriatic arthritis and Reiter's disease), Behchet's disease, Sjogren's syndrome and systemic sclerosis;

(3) skin—psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia areata and vernal conjunctivitis;

(4) gastrointestinal tract—Coeliac disease, proctitis, eosinopilic gastro-enteritis, mastocytosis, Crohn's disease, ulcerative colitis, indeterminate colitis, microscopic colitis, inflammatory bowel disease, irritable bowel syndrome, non-inflammatory diarrhea, food-related allergies which have effects remote from the gut, e.g., migraine, rhinitis and eczema;

(5) central and peripheral nervous system—Neurodegenerative diseases and dementia disorders, e.g. Alzheimer's disease, amyotrophic lateral sclerosis and other motor neuron diseases, Creutzfeldt-Jacob's disease and other prion diseases, HIV encephalopathy (AIDS dementia complex), Huntington's disease, frontotemporal dementia, Lewy body dementia and vascular dementia; polyneuropathies, e.g. Guillain-Barré syndrome, chronic inflammatory demyelinating polyradiculoneuropathy, multifocal motor neuropathy, plexopathies; CNS demyelination, e.g. multiple sclerosis, acute disseminated/haemorrhagic encephalomyelitis, and subacute sclerosing panencephalitis; neuromuscular disorders, e.g. myasthenia gravis and Lambert-Eaton syndrome; spinal disorders, e.g. tropical spastic paraparesis, and stiff-man syndrome: paraneoplastic syndromes, e.g. cerebellar degeneration and encephalomyelitis; CNS trauma; migraine; and stroke.

(6) other tissues and systemic disease—atherosclerosis, Acquired Immunodeficiency Syndrome (AIDS), lupus erythematosus, systemic lupus, erythematosus, Hashimoto's thyroiditis, type I diabetes, nephrotic syndrome, cosinophilia fascitis, hyper IgE syndrome, lepromatous leprosy, and idiopathic thrombocytopenia pupura; post-operative adhesions, and sepsis.

(7) allograft rejection—acute and chronic following, for example, transplantation of kidney, heart, liver, lung, bone marrow, skin and cornea; and chronic graft versus host disease;

(8) cancers—especially non-small cell lung cancer (NSCLC), malignant melanoma, prostate cancer and squamous sarcoma, and tumour metastasis, non melanoma skin cancer and chemoprevention metastases;

(9) diseases—in which angiogenesis is associated with raised CXCR2 chemokine levels (e.g. NSCLC, diabetic retinopathy);

(10) cystic fibrosis;

(11) burn wounds & chronic skin ulcers;

(12) reproductive diseases—for example disorders of ovulation, menstruation and implantation, pre-term labour, endometriosis;

(13) re-perfusion injury—in the heart, brain, peripheral limbs and other organs, inhibition of atherosclerosis.

Thus, the present invention provides a compound of formula (I) or a pharmaceutically acceptable salt thereof for use in therapy.

Thus, the present invention provides the compound of formula (I) or tautomers thereof, or a pharmaceutically-acceptable salt thereof, as hereinbefore defined for use in therapy.

Conveniently the compounds of the invention are used to treat diseases in which the chemokine receptor belongs to the CXC chemokine receptor subfamily, more conveniently the target chemokine receptor is the CXCR2 receptor.

Particular conditions which can be treated with compounds of the invention are cancer, diseases in which angiogenesis is associated with raised CXCR2 chemokine levels, and inflammatory diseases such as asthma, allergic rhinitis, COPD, rheumatoid arthritis, psoriasis, inflammatory bowel diseases, osteoarthritis or osteoporosis. Each condition/disease listed above when taken independently or in any combination represents an independent embodiment of the invention.

The compounds of the invention may also be used to treat diseases in which the chemokine receptor belongs to the CCR chemokine receptor subfamily, more conveniently the target chemokine receptor is the CCR2b receptor.

In a further aspect, the present invention provides a compound of formula (I) or a pharmaceutically acceptable salt thereof as hereinbefore defined for use as a medicament.

In a still further aspect, the present invention provides the use of the compound of formula (I) or a pharmaceutically acceptable salt thereof, as hereinbefore defined, for use as a medicament for the treatment of human diseases or conditions in which modulation of chemokine receptor activity is beneficial.

In a still further aspect, the present invention provides the use of the compound of formula (I) or a pharmaceutically acceptable salt thereof, as hereinbefore defined, for use as a medicament for the treatment of asthma, allergic rhinitis, cancer, COPD, rheumatoid arthritis, psoriasis, inflammatory bowel diseases, osteoarthritis or osteoporosis.

In a further aspect, the present invention provides the use of the compound of formula (I) or a pharmaceutically acceptable salt thereof, as hereinbefore defined in the manufacture of a medicament for use in therapy.

In a still further aspect, the present invention provides the use of the compound of formula (I) or a pharmaceutically acceptable salt thereof, as hereinbefore defined in the manufacture of a medicament for the treatment of human diseases or conditions in which modulation of chemokine receptor activity is beneficial.

In a still further aspect, the present invention provides the use of the compound of formula (I) or a pharmaceutically acceptable salt thereof, as hereinbefore defined in the manufacture of a medicament for the treatment of asthma, allergic rhinitis, cancer, COPD, rheumatoid arthritis, psoriasis, inflammatory bowel diseases, osteoarthritis or osteoporosis.

In a still further aspect, the present invention provides the use of the compound of formula (I) thereof, or a pharmaceutically acceptable salt thereof, as hereinbefore defined in the manufacture of a medicament for the treatment of asthma, allergic rhinitis or COPD.

In a still further aspect, the present invention provides the use of the compound of formula (I), or a pharmaceutically acceptable salt thereof, as hereinbefore defined in the manufacture of a medicament for the treatment of COPD.

In a still further aspect, the present invention provides the use of the compound of formula (I) thereof, or a pharmaceutically acceptable salt thereof, as hereinbefore defined in the manufacture of a medicament for the treatment of asthma.

In the context of the present specification, the term "therapy" also includes "prophylaxis" unless there are specific indications to the contrary. The terms "therapeutic" and "therapeutically" should be construed accordingly.

The invention still further provides a method of treating a chemokine mediated disease wherein the chemokine binds to a chemokine (especially CXCR2) receptor, which comprises administering to a patient a therapeutically effective amount of the compound of formula (I) (or a pharmaceutically acceptable salt thereof as hereinbefore defined.

The invention also provides a method of treating an inflammatory disease, especially asthma, allergic rhinitis, COPD, rheumatoid arthritis, psoriasis, inflammatory bowel diseases, osteoarthritis or osteoporosis, in a patient suffering from, or at risk of, said disease, which comprises administering to the patient a therapeutically effective amount of a compound of formula (I) or a pharmaceutically acceptable salt thereof, as hereinbefore defined.

The invention also provides a method of treating an inflammatory disease, especially asthma, allergic rhinitis or COPD, in a patient suffering from, or at risk of, said disease, which comprises administering to the patient a therapeutically effective amount of a compound of formula (I) or a pharmaceutically acceptable salt thereof, as hereinbefore defined.

For the above-mentioned therapeutic uses the dosage administered will, of course, vary with the compound employed, the mode of administration, the treatment desired and the disorder indicated.

The compound of formula (I) and pharmaceutically acceptable salts thereof may be used on its own but will generally be administered in the form of a pharmaceutical composition in which formula (I) compound/salt (active ingredient) is in association with a pharmaceutically acceptable adjuvant, diluent or carrier. Depending on the mode of administration, the pharmaceutical composition will conveniently comprise from 0.05 to 99% w (percent by weight), more conveniently from 0.05 to 80% w, still more conveniently from 0.10 to 70% w, and even more conveniently from 0.10 to 50% w, of active ingredient, all percentages by weight being based on total composition.

The present invention also provides a pharmaceutical composition comprising the compound of formula (I), or a pharmaceutically acceptable salt thereof, as hereinbefore defined, in association with a pharmaceutically acceptable adjuvant, diluent or carrier.

The invention further provides a process for the preparation of a pharmaceutical composition of the invention which comprises mixing the compound of formula (I), or a pharmaceutically acceptable salt thereof, as hereinbefore defined, with a pharmaceutically acceptable adjuvant, diluent or carrier. The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally. Conveniently the compounds of the invention are administered orally.

In addition to their use as therapeutic medicines, the compounds of formula (I) and their pharmaceutically acceptable salts are also useful as pharmacological tools in the development and standardisation of in vitro and in vivo test systems for the evaluation of the effect of chemokine modulation activity in laboratory animals such as cats, dogs, rabbits, monkeys, rats and mice, as part of the search for new therapeutic agents.

The invention further relates to combination therapies wherein a compound of formula (I) or a pharmaceutically acceptable salt thereof, or a pharmaceutical composition or formulation comprising a compound of formula (I) is administered concurrently or sequentially with therapy and/or an agent for the treatment of any one of asthma, allergic rhinitis, cancer, COPD, rheumatoid arthritis, psoriasis, inflammatory bowel disease, irritable bowel syndrome, osteoarthritis or osteoporosis.

The present invention also provides a pharmaceutical composition comprising the compound of formula (I), or a pharmaceutically acceptable salt thereof, as hereinbefore defined, in association with a pharmaceutically acceptable adjuvant, diluent or carrier.

In addition to their use as therapeutic medicines, the compounds of formula (I) and their pharmaceutically acceptable salts are also useful as pharmacological tools in the development and standardisation of in vitro and in vivo test systems for the evaluation of the effect of chemokine modulation activity in laboratory animals such as cats, dogs, rabbits, monkeys, rats and mice, as part of the search for new therapeutic agents.

The invention further relates to combination therapies wherein a compound of formula (I) or a pharmaceutically acceptable salt thereof, or a pharmaceutical composition or formulation comprising a compound of formula (I) is administered concurrently or sequentially with therapy and/or an agent for the treatment of any one of asthma, allergic rhinitis, cancer, COPD, rheumatoid arthritis, psoriasis, inflammatory bowel disease, irritable bowel syndrome, osteoarthritis or osteoporosis.

In particular, for the treatment of the inflammatory diseases rheumatoid arthritis, psoriasis, inflammatory bowel disease, irritable bowel syndrome, COPD, asthma and allergic rhinitis the compounds of the invention may be combined with agents such as TNF-α inhibitors such as anti-TNF monoclonal antibodies (such as Remicade, CDP-870 and $D_2.E_7$.) and TNF receptor immunoglobulin molecules such as Etanercept (Enbrel), non-selective COX-1/COX-2 inhibitors (such as piroxicam, diclofenac), propionic acids such as naproxen, flubiprofen, fenoprofen, ketoprofen and ibuprofen), fenamates (such as mefenamic acid, indomethacin, sulindac, apazone), pyrazolones (such as phenylbutazone), salicylates (such as aspirin), COX-2 inhibitors (such as meloxicam, celecoxib, rofecoxib, valdecoxib and etoricoxib) low dose methotrexate, lefunomide; ciclesonide; hydroxychloroquine, d-penicillamine, auranofin or parenteral or oral gold. For inflammatory bowel disease and irritable bowel disorder further convenient agents include sulphasalazine and 5-ASAs, topical and systemic steroids, immunomodulators and immunosuppressants, antibiotics, probiotics and anti-integrins.

The present invention still further relates to the combination of the compound of the invention together with a leukotriene biosynthesis inhibitor, 5-lipoxygenase (5-LO) inhibitor or 5-lipoxygenase activating protein (FLAP) antagonist such as zileuton; ABT-761; fenleuton; tepoxalin; Abbott-79175; Abbott-85761; N-(5-substituted)-thiophene-2-alkylsulfonamides; 2,6-di-tert-butylphenol hydrazones; methoxytetrahydropyrans such as Zeneca ZD-2138; the compound SB-210661; pyridinyl-substituted 2-cyanonaphthalene compounds such as L-739,010; 2-cyanoquinoline compounds such as L-746,530; indole and quinoline compounds such as MK-591, MK-886, and BAY x 1005.

The present invention still further relates to the combination of the compound of the invention together with a receptor antagonist for leukotrienes $LTB_4$, $LTC_4$, $LTD_4$, and $LTE_4$ selected from the group consisting of the phenothiazin-3-ones such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of the compound of the invention together with a PDE4 inhibitor including inhibitors of the isoform PDE4D.

The present invention still further relates to the combination of the compound of the invention together with a antihistaminic $H_1$. receptor antagonists such as cetirizine, loratadine, desloratadine, fexofenadine, astemizole, azelastine, and chlorpheniramine.

The present invention still further relates to the combination of the compound of the invention together with a gastroprotective $H_2$ receptor antagonist.

The present invention still further relates to the combination of the compound of the invention together with an $\alpha_1$- and $\alpha_2$-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride.

The present invention still further relates to the combination of the compound of the invention together with anticholinergic agents such as ipratropium bromide; tiotropium bromide; oxitropium bromide; pirenzepine; and telenzepine.

The present invention still further relates to the combination of the compound of the invention together with a $\beta_1$- to $\beta_4$-adrenoceptor agonists such as metaproterenol, isoproterenol, isoprenaline, albuterol, salbutamol, formoterol, salmeterol, terbutaline, orciprenaline, bitolterol mesylate, and pirbuterol; or methylxanthanines including theophylline and aminophylline; sodium cromoglycate; or muscarinic receptor (M1, M2, and M3) antagonist.

The present invention still further relates to the combination of the compound of the invention together with an insulin-like growth factor type I (IGF-1) mimetic.

The present invention still further relates to the combination of the compound of the invention together with an inhaled glucocorticoid with reduced systemic side effects, such as prednisone, prednisolone, flunisolide, triamcinolone acetonide, beclomethasone dipropionate, budesonide, fluticasone propionate, and mometasone furoate.

The present invention still further relates to the combination of the compound of the invention together with an inhibitor of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-12.

The present invention still further relates to the combination of the compound of the invention together with other modulators of chemokine receptor function such as CCR1, CCR2, CCR2A, CCR2B, CCR3, CCR4, CCR5, CCR6, CCR7, CCR8, CCR9, CCR10 and CCR11 (for the C—C family); CXCR1, CXCR3, CXCR4 and CXCR5 (for the C—X—C family) and $CX_3CR1$ for the C—$X_3$—C family.

The present invention still further relates to the combination of the compound of the invention together with antiviral agents such as Viracept, AZT, aciclovir and famciclovir, and antisepsis compounds such as Valant.

The present invention still further relates to the combination of the compound of the invention together with cardiovascular agents such as calcium channel blockers, lipid lowering agents such as statins, fibrates, beta-blockers, ACE inhibitors, Angiotensin-2 receptor antagonists and platelet aggregation inhibitors.

The present invention still further relates to the combination of the compound of the invention together with CNS agents such as antidepressants (such as sertraline), anti-Parkinsonian drugs (such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as donepezil, tacrine, COX-2 inhibitors, propentofylline or metryfonate.

The present invention still further relates to the combination of the compound of the invention together with (i) tryptase inhibitors; (ii) platelet activating factor (PAF) antagonists; (iii) interleukin converting enzyme (ICE) inhibitors; (iv) IMPDH inhibitors; (v) adhesion molecule inhibitors including VLA-4 antagonists; (vi) cathepsins; (vii) MAP kinase inhibitors; (viii) glucose-6 phosphate dehydrogenase inhibitors; (ix) kinin-$B_1$- and $B_2$.-receptor antagonists; (x) anti-gout agents, e.g., colchicine; (xi) xanthine oxidase inhibitors, e.g., allopurinol; (xii) uricosuric agents, e.g., probenecid, sulfinpyrazone, and benzbromarone; (xiii) growth hormone secretagogues; (xiv) transforming growth factor (TGFβ); (xv) platelet-derived growth factor (PDGF); (xvi) fibroblast growth factor, e.g., basic fibroblast growth factor (bFGF); (xvii) granulocyte macrophage colony stimulating factor (GM-CSF); (xviii) capsaicin cream; (xix) Tachykinin $NK_1$. and $NK_3$. receptor antagonists selected from the group consisting of NKP-608C; SB-233412 (talnetant); and D-4418; (xx) elastase inhibitors selected from the group consisting of UT-77 and ZD-0892; (xxi) TNF converting enzyme inhibitors (TACE); (xxii) induced nitric oxide synthase inhibitors (iNOS) or (xxiii) chemoattractant receptor-homologous molecule expressed on TH2 cells, (CRTH2 antagonists).

The compound of the present invention may also be used in combination with osteoporosis agents such as roloxifene, droloxifene, lasofoxifene or fosomax and immunosuppressant agents such as FK-506, rapamycin, cyclosporine, azathioprine, and methotrexate.

The compound of the invention may also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, rofecoxib and etoricoxib, analgesics and intraarticular therapies such as corticosteroids and hyaluronic acids such as hyalgan and synvisc and P2X7 receptor antagonists.

The compound of the invention may also be used in combination with existing therapeutic agents for the treatment of cancer. Suitable agents to be used in combination include:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea, gemcitabine and paclitaxel (Taxol®); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) Agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as IN-(3-chloro-4-fluorophenyl)-7-methoxy-6-(3-morpholinopropoxy)quinazolin-4-amine (gefitinib, AZD 1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166. WO00/40529, WO 00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (genc-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

The invention will now be illustrated but not limited by reference to the following: Specific Description. Examples and Biological Data.

Specific Description

Table 1 below summarises the measured in vitro potency and the measured in vivo dog half life for the compound of the invention.

| Example No. | Potency (pIC$_{50}$) | Half life (dog) (hours) |
|---|---|---|
| 1 (structure) | 8.4 | 3.7 |

A long half life in a pre-clinical species (such as dog) suggests that a substantial half-life in human is attainable (Obach et al, 1997). The measured half life in dog for the compound of the invention is 3.7 hours.

Furthermore, in order to produce the desired biological effect between dosing intervals a compound must exhibit high potency in addition to long half life. The compound of the invention demonstrates the required combination of high potency (pIC$_{50}$ 8.4) and long measured half life in dog (3.7 hours).

Biological Data

Potency (pIC$_{50}$)—Ligand Binding Assay

Human Embryonic Kidney 293 cells (HEK293 cells) from the American Type Culture Collection were transfected with human CXCR2 cDNA (RefSeqNM_001557), previously cloned into the eukaryotic expression vector pIRES-Neo2, (Clontech). Populations of Geneticin (Invitrogen)-resistant cells were selected for stable expression of CXCR2 and clones were generated by dilution cloning (0.3 cells/well) in 96-well tissue culture plates.

Cells of the highest expressing clone (Clone 6, identified by FACS analysis) were harvested, following 24 hour pretreatment with 5 mM sodium butyrate, in 10 ml of ice-cold hypotonic buffer (20 mM HEPES, 1 mM EDTA, 0.1 mM DTT, 0.1 mM Phenyl Methyl Sulphonyl Fluoride and 0.1 mg/L Bacitracin, pH7.4) and left to swell for 10 min. Following centrifugation (200 g, 5 min, 4° C.), cells were resuspended in hypotonic buffer and membranes were prepared using a polytron tissue homogenizer (3×10 second treatments). The homogenate was centrifuged (200 g, 10 min, 4° C.) to remove cell debris and the resultant supernatant was centrifuged at high speed (15,000 g, 60 min, 4° C.). Membranes were resuspended in hypotonic buffer, homogenised 10 times in a Dounce homogeniser and stored at −80° C.

All assays were performed in black, 384-well plates (Greiner). CXCR2 membranes were pre-mixed with lectin biotin for 1 hour on ice. Sphero™ beads (Streptavidin Polystyrene Particles, 6.0-8.0 μm) were washed in phosphate buffered saline (PBS) and pre-coated with the CXCR2 membrane-lectin biotin mix for 30 min, on a rotor, at room temperature. Membrane-coated Sphero™ beads were washed twice in PBS (1900 g, 5 min) and incubated with serial dilutions of compounds, Alexa$^{647}$ IL-8 (Albachem) at 1 nM final assay concentration and assay buffer (Hanks' Balanced Salt Solution (Invitrogen) containing 10 mM HEPES, 0.1% (w/v) Gelatin and 0.25 mg/ml Bacitracin, pH7.4). The assay was conducted in a final volume of 40 μl in the presence of 1.25% (v/v) dimethyl sulphoxide (DMSO). Total binding of Alexa$^{647}$ IL-8 was determined in the absence of competing compound and non-specific binding of Alexa$^{647}$ IL-8 was determined in the presence of 0.3 μM 1-(4-chloro-2-hydroxy-3-sulfamoyl-phenyl)-3-(2,3-dichlorophenyl)urea. The plates were incubated for 2.5 hours at room temperature and then read on a FMAT8200 (Applied BioSystems). pIC$_{50}$ values were determined as the negative logarithm of the molar concentration of compound required for 50% reduction in specific Alexa$^{647}$ IL-8 binding.

Using the above protocol, the compound of the invention was found to have a pIC$_{50}$ value of 8.4.

Dog Half-Life (Measured)

The following describes the methods used to obtain in vivo pharmacokinetic parameters in the male beagle dog. It is applicable for use with any compound but may need modification based on such parameters as solubility, assay sensitivity, anticipated clearance and half-life, when the default formulation, dose level or sampling intervals may be inappropriate. The method described here represents a standard approach from which justified and documented modifications can be made.

Dose Preparation

A standard dose solution of 1 mg·mL$^{-1}$ was prepared. The recommended dose vehicle (if the compound was not sufficiently soluble in isotonic saline) was 10%/o DMSO:90% sterile water or saline with pH adjustment using 1 M HCl or NaOH. The required mass of compound was dissolved in DMSO before addition of the water. The concentration of the compound in the dose solution was assayed by diluting an aliquot (in triplicate) to a nominal concentration, spiking 10 μl of this into 50 μl blank plasma and analysing along with the test samples.

Dosing

Compounds were administered intravenously via a 30 minute infusion into the caudal vein to a pair of (11-15 kg) beagle dogs (approximately 1 mL·kg$^{-1}$). Delivered doses were estimated by weight loss.

Sample Collection and Analysis

Blood samples (~1 ml) were taken into EDTA treated sampling tubes and plasma was prepared by centrifugation (3 minutes at 13000 rpm) soon after sample collection. Samples were taken at pre determined times over 24 hours (e.g. 0, 5, 15, 30, 35, 45, 60, 90, 120, 180, 240, 300, 360, 420, 720, 1440 minutes). The concentration of the analyte(s) was quantitatively determined in plasma by mass spectrometry. Where appropriate, test samples were diluted with blank plasma in order to ensure they were within the range of the standard curve.

Preparation of Standards and QCs

Standard and quality control stock solutions were prepared from separate weighings of compound prepared at 1 mg/ml in methanol and then further diluted to 100 µg/ml. The standards and QC stocks were diluted manually in methanol and spiked into plasma according to the following table:

| | Serial Dilution Program | | 100 µg/ml stock | |
|---|---|---|---|---|
| Solution | Volume stock (µL) | Volume Diluent (µL) | Std Conc. (ng/mL) | QC Conc. (ng/mL) |
| A | 90 of initial stock | 810 | 2000 | — |
| B | 150 of A | 150 | 1000 | 1000 |
| C | 150 of B | 150 | 500 | — |
| D | 150 of C | 150 | 250 | — |
| E | 150 of D | 225 | 100 | — |
| F | 150 of E | 150 | 50 | 50 |
| G | 150 of F | 150 | 25 | — |
| H | 150 of G | 225 | 10 | — |
| I | 150 of H | 150 | 5 | — |
| J | 150 of I | 150 | 2.5 | 2.5 |
| K | 150 of J | 225 | 1 | — |

10 µl of each of the above solutions A-K, produced by serial dilution of the standard stock, and 10 µL of solutions B, F and J, produced by serial dilution of the QC stock, were added to 96 well 1.2 mL polypropylene tubes containing 50 µl blank plasma. The final concentrations of the standard curve and QC samples produced are shown in the table above.

Preparation of Samples

To each of the test samples, dose tests, standards and QCs 100 µL (90 µl for dose tests, standards and QCs) of methanol was added followed by 100 µl of internal standard. The samples were then capped, mixed by repeated inversion and then centrifuged at 3500 rpm for 20 minutes. Aliquots (120 µL) of each sample were transferred into a microtitre plate ready for analysis via HPLC/MS-MS.

Mass Spectrometry

A TSQ700 or a TSQ or SSQ7000 mass spectrometer with a HP1100 HPLC system was used. The sources used were APCI or ESI. Standard and QC samples covering the range of concentrations found in the test samples were expected to be within 25% of the nominal concentration.

Results

Pharmacokinetic data analysis and tabulation was achieved using a non-compartmental analysis tool and Excel. Briefly, the natural log of the plasma concentrations was plotted against time to show the concentration-time profile. The elimination half-life, which is defined as the time required for the concentration to deplete by half once the initial distribution phase is completed (pseudo steady state), was determined individually for each animal using a minimum of 4 data points. The associated area under the curve (AUC) was confirmed to be >50% to ensure the therapeutically relevant half-life was estimated. Where the PK profile was tri-phasic due to suspected entero-hepatic recirculation the terminal phase was removed from the profile for calculation of the PK parameters including half-life. Quoted half-life values represent a mean of a minimum of two beagle dogs.

Using the above protocol, the compound of the invention was found to have a half-life in dog of 3.7 hours.

Measurement of Human Hepatic Intrinsic Clearance ($CL_{int}$)

For the majority of drugs, a large component of their plasma clearance is contributed by hepatic metabolism. Intrinsic clearance ($CL_{int}$) is a measure of the potential of a compound to undergo metabolism and can be related to hepatic clearance in vivo from a consideration of plasma protein binding and liver blood flow. Therefore, $CL_{int}$ may be used as a key parameter in predicting the half-life of a compound in humans.

Test Description

This following description outlines a method for estimating intrinsic clearance ($CL_{int}$) from human hepatocyte incubations using suspension buffer containing no HSA (human serum albumin) and maintaining physiological conditions of pH 7.4.

In order for the skilled person to reproduce the operating characteristics of this test procedure, reference is made to specific suppliers and catalogue numbers for the reagents used at the time of initial validation and finalisation of the test procedure. This does not preclude substitution with suitable alternative reagents with either a documented comparable specification or following experimental confirmation that substitution does not significantly affect the operating characteristics of the assay.

Hepatocyte Isolation and Estimation of Yield and Viability

Cryopreserved human hepatocytes (multiple donors) were purchased from Cellzdirect (Carlsbad, U.S.) and stored in liquid nitrogen. Cells were resuspended in protein-free hepatocyte suspension buffer (recipe: 2.34 g Na HEPES, 0.4 g D-fructose, DMEM (1 L powder equivalent, Sigma; w/l g·l$^{-1}$ glucose, w/Na pyruvate, w/o NaHCO$_3$, w/o phenol red), made up to 1 L with Milli-Q water, pH to 7.4 with 1 M HCl). The cryopreserved cells were thawed to prepare for use as follows: each vial of cells was immersed in a waterbath at 37° C. and gently shaken for approximately 2 minutes until all the ice had melted. The thawed cell suspension was then added to 15 ml pre-warmed hepatocyte suspension buffer in a round bottomed centrifuge tube and gently mixed by inverting the centrifuge tube. The cell suspension was centrifuged at 600 rpm at ambient temperature (~26° C.) for 5 minutes and the supernatant aspirated and discarded. The pellet was gently resuspended in hepatocyte buffer (1.5 ml per vial of cells) to give a homogeneous cells suspension.

An aliquot of cell suspension (0.2 mL) was diluted with 0.2 ml protein-free suspension buffer. To the diluted cells was added 0.2 mL trypan blue solution (0.4% w/v) followed by gentle mixing. After 1 min, a pasteur pipette was used to withdraw a sample and fill an Improved Neubauer Counting Chamber by capillary action. The cells were then counted (central square only) using an inverted microscope, viable cells being able to exclude the dye and non-viable cells being stained. The percentage of viable cells in the preparation was calculated thus:

$$\frac{\text{Viable cell count}}{\text{Total cell count}} \times \frac{100}{1} = \% \text{ viability}$$

The concentration of viable cells was calculated:

Viable cells ml$^{-1}$=Viable cell count×10$^4$×3×50

The counting procedure was performed in duplicate.

The cell suspension was diluted with an appropriate volume of protein-free suspension buffer to give the required concentration of viable cells and stored on ice for up to 1 h prior to use.

Test Procedure

The test compound to be incubated was added from a concentrated stock solution of 0.1 mM in DMSO (1% v/v final solvent concentration) to an appropriate volume (0.3 ml) of protein-free suspension buffer in a suitable vial. An appropriate volume of cells (>0.3 ml) at a concentration of 2×10$^6$ cells·ml$^{-1}$ (twice the final incubation cell concentration, viability>85% by trypan blue exclusion) was placed in a separate vial and both vials were pre-incubated in a water bath at 37° C.

After 5 min pre-incubation an appropriate volume of the cells (0.3 ml) was added to the buffer and compound in order to give a final cell concentration of 1×10$^6$ cells·ml$^{-1}$ and compound concentration of 1 µM and the reactions allowed to proceed.

At appropriate time points (e.g. 5, 15, 30, 45, 60, 75, 90 and 120 min), aliquots (40 µl) were taken out of the incubation mix and added to 3 volumes of methanol to terminate the reactions and denature the hepatocytes. Control incubations were also conducted in which cells were omitted. Once the incubations had been quenched, the samples were mixed, stored at −20° C. or below for 2 h to aid protein precipitation and then centrifuged for 15 min at 3600 rpm and 4° C. The supernatants were transferred to micro titre plates and analysed by HPLC-MSMS using the following method as a suitable starting point:

Solvents: A: 0.1% formic acid in methanol and B: 0.1% formic acid in water (v/v)
Column: Waters Xterra C$_{18}$ 20×3.9 mm, 3.5 µm
Flow rate: 1.5 ml·min$^{-1}$
Gradient: 0% B for 0.3 minutes, 0% to 100% B over 0.7 minutes, held at 100% B for 0.2 minutes, 100% to 0% B over 0.01 minutes.

Data Analysis and Calculation Methods

The resultant peak areas of the incubated compounds are taken into an Excel spreadsheet and a plot of ln [residual concentration] versus time produced and from the residual slope t½ estimated. The treatment of the data was then akin to a one-compartment, pharmacokinetic model and using the elimination rate constant (k)=ln(2)/t½, an equation expressing CL$_{int}$ in terms of t½ can be derived as given in the equation below, where volume is expressed in ml 10$^6$ cells$^{-1}$ $$CL_{int} = \frac{\text{Volume} \times 0.693}{t_{1/2}}$$

The t½ and CL$_{int}$ for the loss of the parent compound from the incubation was then determined.

Using the above protocol, the compound of the invention was found to have a human hepatocyte intrinsic clearance of 2.9 (±0.94) µL/min/10$^6$ cells.

A low metabolic clearance in human typically results in significantly longer human half-life. Methods of predicting metabolic clearance in humans are well-known to those skilled in the art. For example, human metabolic clearance may be predicted from the measured in vitro human hepatocyte intrinsic clearance data, measured in vitro human plasma protein binding data and measured distribution coefficient (log D$_{7.4}$) (see in particular Austin et al (2005), *Drug Metab. Dispos.*, 33, 419-425; and Riley et al (2005), *Drug Metab. Dispos.*, 33, 1304-1311).

Measurement of Human Plasma Protein Binding (hPPB)

The extent of binding of a drug to plasma proteins is a crucial factor in determining in vivo potency and pharmacokinetics. The method used for determining the extent of plasma protein binding involves equilibrium dialysis of the compound between plasma and buffer at 37° C. The concentrations of compound in the plasma and buffer are then determined using high pressure liquid chromatography (HPLC) with mass spectroscopy (MS) detection. The dialysis method involves the use of mixtures of up to 10 compounds simultaneously. At the concentrations used in the assay, there is no significant difference in the results when compounds are run singly or in mixtures.

Test Description

Membranes (molecular weight cut-off 5000) were first prepared by soaking in the dialysis buffer for a minimum of 1 hour. The dialysis membranes were then mounted into the dialysis cells.

Stock solutions of compounds in dimethylsulphoxide (DMSO) were prepared. This, and all subsequent liquid handling steps, were normally carried out with a Tecan liquid handling robot. Mixtures of up to five compounds were used. The concentration of each compound in a mixture was normally 1 mM. The mixtures were chosen such that each mixture contains compounds that all have at least a 5 unit difference in molecular weight from one another.

Frozen plasma (EDTA anticoagulant) was normally used for the human plasma binding experiment. The pH of the plasma was adjusted to 7.4 using 1 M HCl immediately before use.

The stock DMSO solution of compounds (7.5 µL) was then added to the dialysis cells along with plasma (750 µl). This was done in duplicate for each mixture. This gave a 1% DMSO in plasma solution with each compound at a concentration of 10 µM (if the stock solution was the standard 1 mM). The dialysis cells were then sealed, secured in a Dianorm rotator unit and equilibrated for 18 hours at 37° C. While the dialysis cells were being equilibrated, the DMSO stock solutions were used for generating optimised HPLC/MS methods for use in the final analysis of the plasma and buffer samples.

After equilibration, the cells were opened and a Tecan liquid handling robot was used to remove aliquots from the plasma and buffer sides of each of the dialysis cells. Blank plasma was then added to the buffer samples and buffer added to the plasma samples such that each sample was in a matrix of 6-fold diluted plasma. Standards were then prepared from the DMSO stock solutions and blank 6-fold diluted plasma. The concentrations of the four standards were normally 50 nM, 150 nM, 500 nM and 2500 nM.

The samples and standards were then analysed using HPLC with MS detection, which allows deconvolution of the mixtures of compounds. The HPLC method involved a forward flushing column switching technique that allows direct injection of the diluted plasma.

Calculation of Results

The chromatograms were processed using MassLynx software that automatically calculates a calibration curve for each compound in a mixture and then interpolates the concentrations of buffer and plasma samples. These concentrations still need corrections for the dilution of the plasma. The percentage bound was calculated from the MassLynx data using the following equation:

$$\% \text{ bound} = 100 - 100 \left( \frac{1.2 \times \text{Buffer concentration}}{6 \times \text{Plasma concentration}} \right)$$

The factor of 1.2 in the numerator accounts for the small dilution of the aqueous samples with plasma. The factor of 6 in the denominator serves to correct for the 6-fold dilution of the plasma samples with buffer.

The % free (100-% bound) for each compound was calculated from the concentration data, and then recorded.

Using the above protocol, the compound of the invention was found to have a human plasma protein binding (% free) of 0.11 (±0.05).

Measurement of Distribution Coefficient at pH 7.4 (Log $D_{7.4}$)

Compounds of interest (1 mg) were dispensed into individual 1-mL polypropylene vials, held within a 96-well plate along with 1-octanol (700 μL), and presaturated with 0.02 M phosphate buffer (pH 7.4). The plate was then shaken overnight followed by centrifugation (800 g for 15 min) to sediment any undissolved solids. Up to 24 mixtures of 10 compounds (or less) were then prepared by pooling the 1-octanol solutions (100 μL) into a plate of 12-mL glass sample tubes. The pooling of solutions was performed using a bespoke algorithm, such that none of the compounds in each mixture had a mono-isotopic mass within 2 Daltons of each other, allowing facile resolution of the components of the mixture during the MS quantification. The pooling of compounds was performed robotically and controlled using automatically generated bespoke work lists. If a mixture contained less than 10 compounds, then 1-octanol (presaturated with 0.02 M phosphate buffer [pH 7.4]) was added to make up the total volume of the 1-octanol phase to 1 mL. 1-Octanol-saturated phosphate buffer (0.02 M, pH 7.4, 2 mL) was then added to each mixture before shaking (450 rpm for 30 min) and centrifugation (800 g for 15 min). The final 1-octanol and aqueous phases of each partition mixture were then robotically separated. The first step was to take an aliquot of the 1-octanol phase (20 μL) for LC analysis using a 1-octanol liquid class. The second step was to remove the excess 1-octanol phase to expose the aqueous phase. This was performed by repeat aspirations of the 1-octanol from various positions within the sample tubes. The final step in the separation was to take an aliquot of the aqueous phase (50 μL). The 1-octanol and aqueous aliquots were serially diluted using DMSO to give the final samples for LC/MS analysis. Five sequential dilutions were made of each final 1-octanol phase, covering a 10 000-fold range in concentration. The MS peak areas from these solutions were used to generate a log(peak area) against log(relative concentration) calibration line. Three sequential dilutions of each final aqueous phase covering a 100-fold concentration range were also prepared, and an LC/MS peak area was selected from one of these three dilutions that best fitted within the range of the calibration line, allowing interpolation of the relative concentration. To minimize the extent of carryover, the order of LC/MS analysis began with the least concentrated dilution of the 1-octanol followed by subsequent more concentrated dilutions, followed by two blank injections and then the dilutions of the aqueous phase in increasing concentration. Log $D_{7.4}$ was calculated from the ratio of one of the 1-octanol relative concentrations to the interpolated aqueous relative concentration after correcting for the extent of dilution of both the 1-octanol and aqueous solutions.

Using the above protocol, the compound of the invention was found to have a Log $D_{7.4}$ of 1.9.

REFERENCE EXAMPLE

The invention will now be illustrated by the following non-limiting Examples and with reference to the enclosed Figures.

The following abbreviations may be used:
DSC Differential scanning calorimeter
DMSO Dimethyl sulfoxide
g Gram(s)
HPLC High performance liquid chromatography
LCMS Liquid chromatography-mass spectroscopy
mL Milliliter(s)
MTBE Methyl tert-butyl ether
MTDSC Modulated temperature differential scanning calorimeter
NMP N-Methylpyrrolidone
TFA Trifluoroacetic acid
THF Tetrahydrofuran
TMBA 3,4,5-trimethoxybenzoic acid
XRPD X-Ray powder diffraction When given, $^1$H NMR spectra were recorded on Bruker Avance 600 (600 MHz), a Bruker DRX 500 (500 MHz), a Bruker 300 (300 MHz) or a Varian UnityInova 500 MHz, 400 MHz or 300 MHz instrument. Either the central peaks of chloroform-d (CDCl$_3$; $\delta_H$ 7.27 ppm), dimethylsulfoxide-d$_6$ (d$_6$-DMSO; $\delta_H$ 2.50 ppm) or methanol-d$_4$ (CD$_3$OD; $\delta_H$ 3.31 ppm), or an internal standard of tetramethylsilane (TMS; $\delta_H$ 0.00 ppm) were used as references. Sample solutions may also contain an internal standard (for example maleic acid, 2,3,5,6-tetrachloronitrobenzene or benzyl benzoate) for assay determination and/or added trifluoroacetic acid, to move exchangeable proton signals (e.g. from maleic acid) away from analyte resonances. Spectral data is reported as a list of chemical shifts (δ, in ppm) with a description of each signal, using standard abbreviations (s=singlet, d=doublet, m=multiplet, t=triplet, q=quartet, br=broad, etc.). It is well known in the art that chemical shifts and J-coupling constants may vary slightly as a result of sample preparation differences, for example analyte concentration and whether or not additives (for example NMR assay standards or trifluoroacetic acid) are included.

Large scale reactions were carried out in stainless steel or glass-lined steel reactors fitted with heat transfer jackets and serviced with appropriate ancillary equipment.

Mass spectra were recorded on an Agilent MSD (+ve and −ve APCI and/or electrospray (e.g. in multimode)) or a Waters Micromass ZQ (+ve and −ve electrospray) following analytical HPLC. Where values for m/z are given, generally only ions which indicate the parent mass are reported, and the mass ions quoted are the positive or negative mass ions: [M]$^+$, [M+H]$^+$, [M−H]$^-$ or [M+2H-BOC]$^+$.

The title and sub-title compounds of the examples and preparations were named using the IUPAC name program Struct=Name 9.0.7 from CambridgeSoft Corporation.

High Performance Liquid chromatography (HPLC) was performed on reversed phase columns packed with octadecyl bonded silica. HPLC instruments equipped with UV detectors (λ=230 nm) and gradient pumps were used. Stationary phase particle size, column dimensions, mobile phases (acetonitrile and water, pH adjusted with trifluoroacetic acid), gradient timetables, flow rates and temperature suitable for the specific analyses were used. Sample solutions were prepared at a main analyte concentration of approximately 0.5 mg mL$^{-1}$ using suitable diluents.

Unless stated otherwise, starting materials were commercially available. All solvents and commercial reagents were of laboratory grade and were used as received. All operations were carried out at ambient temperature, i.e. in the range 17 to 28° C. and, where appropriate, under an atmosphere of an inert gas such as nitrogen. Starting material (E)-but-2-en-1-ol was dried over 3 A molecular sieves prior to use.

Analytical HPLC was carried out using either a Waters XBridge™ C8 3.5 μm column eluting with a gradient of acetonitrile in either 0.1% aqueous trifluoroacetic acid, 0.1% aqueous formic acid, 0.1% aqueous ammonium acetate or 0.1% aqueous ammonia; a Waters XBridge™ C18 3.5 μm column with a gradient of acetonitrile in 0.1% aqueous ammonia; a Waters Symmetry™ C18 3.5 μm column with a gradient of acetonitrile in 0.1% aqueous trifluoroacetic acid; a Waters Sunfire™ C8 3.5 μm column with a gradient of acetonitrile in 0.1% aqueous trifluoroacetic acid; a Phenomenex Gemini™ C18 3 μm column with a gradient of acetonitrile in 0.1% aqueous trifluoroacetic acid; a Polaris Amide C18 3.5 μM column eluting with a gradient of methanol in 0.1% aqueous formic acid; or an Ace Phenyl 3.5 μm column eluting with a gradient of methanol in 0.1% aqueous formic acid. UV spectra of the eluted peaks were measured using a diode array on an Agilent 1100® system, or equivalent;

Chiral analytical GC was carried out using Agilent 6890 series GC with split/splitless injector using either a ChromPak Chiraldex CB column (25 m×0.25 mm with 0.25 μm phase thickness) or a ChromPak Chiraldex CB column (25 m×0.32 mm with 0.25 μm phase thickness). Spectra of the eluted peaks were recorded using a flame ionisation detector. All samples were derivatised by acetic anhydride or (N,O-bis(trimethylsilyl)trifluoroacetamide) prior to GC-analysis.

Chiral analytical HPLC was carried out using an AD-H Chiral Pak 5 μm column eluting with a 25% ethanol in isohexane. UV spectra of the eluted peaks were measured using a diode array on an Agilent 1100® system, or equivalent.

Water analysis was performed by Karl-Fischer titration.

X-Ray powder diffraction analysis (XRPD) were performed on samples prepared according to standard methods, for example those described in Giacovazzo, C. et al (1995), *Fundamentals of Crystallography*, Oxford University Press; Jenkins, R. and Snyder, R. L. (1996), *Introduction to X-Ray Powder Diffractometry*, John Wiley & Sons, New York; Bunn, C. W. (1948), *Chemical Crystallography*, Clarendon Press, London; or Klug, H. P. & Alexander, L. E. (1974), *X-ray Diffraction Procedures*, John Wiley and Sons, New York. X-ray analyses were performed using a PANalytical X'Pert machine in 2Ø-Ø configuration or a PANalytical Cubix machine in Ø-Ø configuration over the scan range 2° to 40° 2Ø with 100-second exposure per 0.02° increment. The X-rays were generated by a copper long-fine focus tube operated at 45 kV and 40 mA. The wavelength of the copper X-rays was 1.5418 Å. The Data was collected on zero background holders on which ~2 mg of the compound was placed. The holder was made from a single crystal of silicon, which had been cut along a non-diffracting plane and then polished on an optically flat finish. The X-rays incident upon this surface were negated by Bragg extinction.

It is known in the art that an X-ray powder diffraction pattern may be obtained which has one or more measurement errors depending on measurement conditions (such as equipment, sample preparation or machine used). In particular, it is generally known that intensities in an X-ray powder diffraction pattern may fluctuate depending on measurement conditions and sample preparation. For example, persons skilled in the art of X-ray powder diffraction will realise that the relative intensities of the peaks may vary according to the orientation of the sample under test and on the type and setting of the instrument used. The skilled person will also realise that the position of reflections can be affected by the precise height at which the sample sits in the diffractometer and the zero calibration of the diffractometer. The surface planarity of the sample may also have a small effect. Hence a person skilled in the art will appreciate that the diffraction pattern data presented herein is not to be construed as absolute and any crystalline form that provides a powder diffraction pattern substantially identical to those disclosed herein fall within the scope of the present disclosure. Generally, a measurement error of a diffraction angle in an X-ray powder diffraction pattern is typically plus or minus 0.2° 2-theta.

Melting point was determined by Differential Scanning Calorimetry (DSC) using standard methods, for example those described in Höhne, G. W. H. et al (1996), *Differential Scanning Calorimetry*, Springer, Berlin. The calorimetric response of a test sample to increasing temperature was investigated using a TA Q2000 Differential Scanning Calorimeter, with aluminium pans. The sample weights varied between 0.5 to 5 mg. The procedure was carried out under a flow of nitrogen gas (50 ml/min) and the temperature studied from 25 to 300° C. at a constant rate of temperature increase of 10° C. per minute. Where a melting point is quoted, this refers to the onset temperature of the melting endotherm.

A person skilled in the art will appreciate that slight variations in the melting point measured by DSC may occur as a result of variations in sample purity, sample preparation and the measurement conditions (e.g. heating rate). It will be appreciated that alternative readings of melting point may be given by other types of equipment or by using conditions different to those described hereinafter. Hence the melting point and endotherm figures quoted herein are not to be taken as absolute values and such measurement errors are to be taken into account when interpreting DSC data. As a skilled person will realise, melting point can vary with sample purity and degree of crystallinity of the sample. Even low levels of impurities can affect the measured melting point. Therefore, the melting points disclosed herein may vary by ±5° C. from the values quoted herein and reference to a substance having a melting point of "about" are to be interpreted as having a value of ±5° C. from the values quoted. It is to be understood that references to melting points disclosed herein refer to the onset temperature of the melting endotherm. A person skilled in the art can use routine optimization/calibration to set up instrumental parameters for a differential scanning calorimeter so that data comparable to the data presented herein may be collected.

Example 1

N-(6-((2R,3S)-3,4-Dihydroxybutan-2-yloxy)-2-(4-fluorobenzylthio)pyrimidin-4-yl)-3-methylazetidine-1-sulfonamide

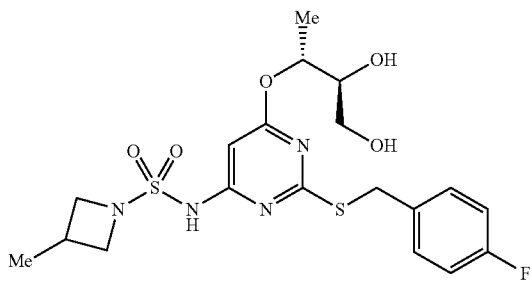

i) 2-(4-Fluorobenzylthio)pyrimidine-4,6-diol

Sodium acetate (113 g) was added to a suspension of 2-mercaptopyrimidine-4,6-diol (80 g) in water (900 mL) at room temperature. A solution of 1-(bromomethyl)-4-fluorobenzene (105 g) in acetonitrile (90 mL) was added dropwise over 2 hours. The reaction was allowed to stir for 20 hours before the suspension was filtered and washed with water (3×) and isohexane (3×). The solid was dried in vacuo for 2 hours and azeotroped with toluene (3×) to afford the sub-title product (125 g) as a white solid.
$^1$H NMR (500 MHz, $d_6$-DMSO) δ 11.62 (s, 2H), 7.57-7.36 (m, 2H), 7.14 (dd, J=6.0, 14.8 Hz, 2H), 5.18 (s, 1H), 4.37 (d, J=6.5 Hz, 2H).

ii) 4,6-Dichloro-2-(4-fluorobenzylthio)pyrimidine

Phosphorus oxychloride (92 mL) was added to a suspension of the sub-title product of step (i) (100 g) and benzyltriethylammonium chloride (9 g) in dimethoxyethane (500 mL) and heated at reflux for 10 hours. The reaction was carefully poured onto stirred ice-water, partitioned between water (400 mL) and ethyl acetate (400 mL) and the organics recovered, dried over magnesium sulfate, filtered and evaporated. The crude product was purified by flash silica chromatography, elution gradient 1-40% dichloromethane in isohexane. Pure fractions were evaporated to dryness to afford the sub-title product (86 g) as a red oil.
$^1$H NMR (500 MHz, CDCl$_3$) δ 7.46-7.34 (m, 2H), 7.08-6.94 (m, 3H), 4.34 (s, 2H).

iii) 4-Chloro-6-((R)-1-((S)-2,2-dimethyl-1,3-dioxolan-1-yl)ethoxy)-2-(4-fluorobenzylthio)pyrimidine The sub-title product of step (ii) (85.7 g) and 60% sodium hydride (14.2 g) were suspended in tetrahydrofuran (1000 mL) and cooled in ice/water for 30 minutes. A solution of (R)-1-((S)-2,2-Dimethyl-1,3-dioxolan-4-yl)ethanol (Intermediate A) in 2-methyltetrahydrofuran (53% w/v) (104 mL) was added dropwise over 20 minutes and the reaction was stirred at 0° C. to room temperature for 20 hours. The reaction was partitioned between water (500 mL) and ethyl acetate (500 mL). The aqueous was re-extracted with ethyl acetate (2×500 mL) and the combined organics were dried and evaporated in vacuo. The crude material was purified by flash silica chromatography with gradient elution 0-30% ethyl acetate in isohexane using Isolera LS. Pure fractions were evaporated to dryness to afford to afford the sub-title product (94 g) as a yellow oil.
$^1$H NMR (500 MHz, CDCl$_3$) δ 7.43-7.35 (m, 2H), 7.04-6.95 (m, 2H), 6.41 (d, J=5.3 Hz, 1H), 5.27-5.17 (m, 1H), 4.33 (s, 2H), 4.20-4.15 (m, 1H), 4.07-4.02 (m, 1H), 3.83-3.76 (m, 1H), 1.39 (dd, J=6.9, 27.4 Hz, 6H), 1.31 (d, J=6.3 Hz, 3H).

iv) N-(6-((R)-1-((S)-2,2-Dimethyl-1,3-dioxolan-4-yl)ethoxy)-2-(4-fluorobenzyl-thio)pyrimidin-4-yl)-3-methylazetidine-1-sulfonamide A solution of the sub-title product of step (iii) (94 g) dissolved in dioxane (700 mL) was treated with 3-methylazetidine-1-sulfonamide (Intermediate B) (42.5 g), potassium carbonate (65.1 g), dicyclohexyl(2',4',6'-triisopropylbiphenyl-2-yl)phosphine (11.2 g) and tris(dibenzylideneacetone)dipalladium(0) (10.8 g) under nitrogen. The resulting mixture was stirred at 100° C. for 60 minutes. The reaction mixture was diluted with water (500 mL) and extracted with ethyl acetate (500 mL). The organics were dried over magnesium sulfate, filtered and evaporated in vacuo to afford crude product. The crude product was purified by flash silica chromatography with elution 30% ethyl acetate in isohexane. Pure fractions were evaporated to dryness to afford the sub-title product (98 g) as a red oil.
m/z [M+H]$^+$=513 (calc=512) (APCI)

v) N-(6-((2R,3S)-3,4-Dihydroxybutan-2-yloxy)-2-(4-fluorobenzylthio)pyrimidin-4-yl)-3-methylazetidine-1-sulfonamide The sub-title product of step (v) (98 g) was stirred in dichloromethane (200 mL) at 0° C. and trifluoroacetic acid (200 mL) added. The reaction was allowed to warm to room temperature and was stirred for a further 18 hours (formed the TFA ester of the alcohol). The volatiles were removed in vacuo and the residue diluted in methanol (20 mL) and treated with 7 M ammonia in methanol (100 mL). The solution was stirred for 20 minutes and then evaporated to dryness to afford crude product. The crude product was purified by flash silica chromatography with gradient elution 50% to 100% ethyl acetate in isohexane. Pure fractions were evaporated to afford the title product as a white solid which was crystallised from acetonitrile to give a white crystalline solid (46.8 g).
m/z [M+H]$^+$=473 (calc=472) (APCI)
$^1$H NMR (500 MHz, $d_6$-DMSO) δ 11.06 (s, 1H), 7.49 (dd, 2H), 7.13 (t, 2H), 6.09 (s, 1H), 5.28-5.18 (m, 1H), 4.93 (d, 1H), 4.65 (t, 1H), 4.37 (q, 2H), 3.97 (t, 2H), 3.70-3.60 (m, 1H), 3.58-3.49 (m, 2H), 3.37 (t, 2H), 2.59 (td, 1H), 1.20 (d, 3H), 1.09 (d, 3H).

Crystals of the title product of Example 1 have been analysed by XRPD. The results are shown in FIG. 1 and some of the characteristic peaks in the XRPD-diffractogram are tabulated below (RI represents relative intensity). A number of weak and very weak peaks have been omitted from the table. Due to preferred orientation effects some of the weak omitted peaks may become more significant.

| Position °2-Theta | RI |
|---|---|
| 8.5 | vs |
| 9.7 | vs |

-continued

| Position °2-Theta | RI |
|---|---|
| 10.6 | s |
| 12.9 | w |
| 16.1 | m |
| 17.1 | s |
| 19.9 | vs |
| 21.1 | m |
| 21.2 | s |
| 23.3 | w |
| 23.5 | w |
| 24.0 | w |
| 25.7 | w |

Abbreviations
vs = very strong;
s = strong;
m = medium;
w = weak

Figure 2:
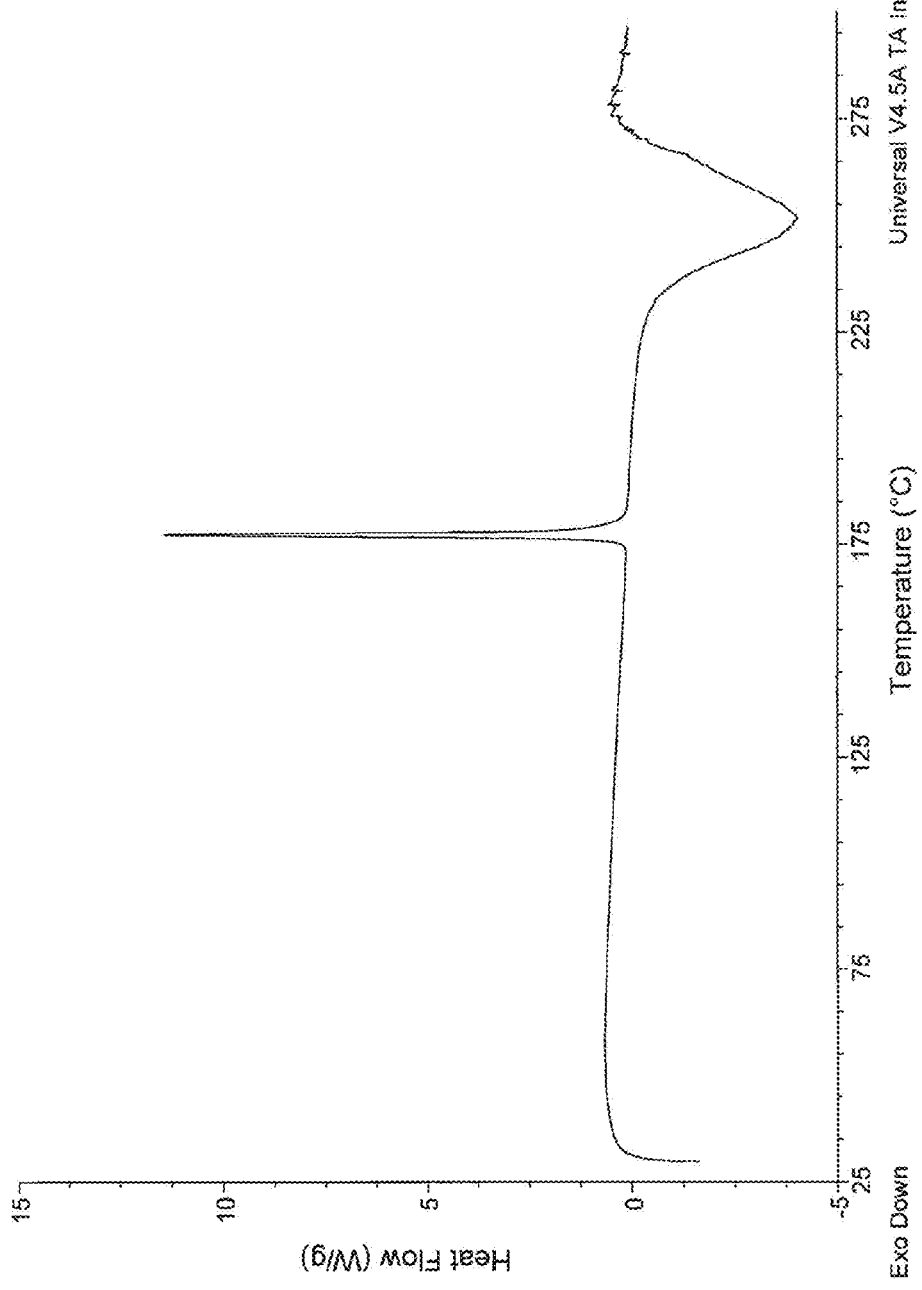
FIG. 2 shows Differential scanning calorimetry profile of Form A of N-(6-((2R,3S)-3,4-Dihydroxybutan-2-yloxy)-2-(4-fluorobenzylthio)pyrimidin-4-yl)-3-methylazetidine-1-sulfonamide.

The differential scanning calorimetry profile of the title product of Example 1 is shown in FIG. 2.

Intermediate A (R)-1-((S)-2,2-Dimethyl-1,3-dioxolan-4-yl)ethanol

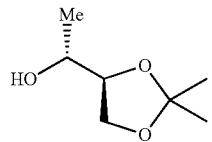

i) 5,6-O-Isopropylidene-L-ascorbic acid

To a mixture of L-ascorbic acid (65 kg, 369 mol), acetone (283 kg) and 2,2-dimethoxypropane (46 kg, 443 mol) was charged p-toluenesulfonic acid (1.1 kg, 5.5 mol). Temperature was adjusted to 25±5° C. The slurry was stirred for 2 hours, during which time nitrogen was frequently flushed through the bottom valve to prevent material from settling at the bottom of the reactor. NMR analysis (solvent: $D_2O$) then showed 98.5% conversion.

Heptanes (222 kg) were charged and the temperature adjusted to 5±5° C. The reaction mixture was stirred for at least 30 minutes before filtering. Remains of the acetonide product in the reactor were rinsed onto the filter cake using the mother liquors. The filter cake was washed with heptanes (111 kg) and dried at 50° C. to give 5,6-O-isopropylidene-L-ascorbic acid (73 kg, 336 mol) as an almost white powder. Yield: 91%.

$^1$H NMR (400 MHz, $d_6$-DMSO, with maleic acid and TFA) δ 4.71 (d, J=3.0 Hz, 1H), 4.28 (m, 1H), 4.11 (dd, J=7.0, 8.4 Hz, 1H), 3.90 (dd, J=6.3, 8.4 Hz, 1H), 1.27 (s, 6H).

ii) (R)-Methyl 2-((S)-2,2-dimethyl-1,3-dioxolan-4-yl)-2-hydroxyacetate 5,6-O-Isopropylidene-L-ascorbic acid (58.8 kg, 272 mol) was charged to sodium hydroxide solution (27.5 kg, 50%, 340 mol) diluted with water (294 kg) and the temperature was adjusted to 30±5° C. Sodium bicarbonate (57 kg, 680 mol) was charged and the mixture was agitated for 15 minutes before the temperature was increased to 40±5° C. Hydrogen peroxide 35% (55 kg, 562 mol) was added to the mixture at 35-60° C. over a period of more than 60 minutes. The reaction mixture was agitated for two hours before NMR analysis (solvent: $D_2O$) showed <1% residual starting material.

Sodium sulfite (4.2 kg, 33 mol) was charged to the reactor and after stirring for 30 minutes, a test for peroxides was negative.

After charging more sodium bicarbonate (34 kg, 408 mol), the mixture was heated to 70±5° C. and agitated for at least one hour before NMR analysis (solvent: $D_2O$) showed 98.5% conversion to the next intermediate, (2R)-[(4S)-2,2-dimethyl-1,3-dioxolan-4-yl](hydroxy)ethanoic acid.

Approximately 150 L of water was stripped off under reduced pressure before filtering off salts. The filter cake was washed with water (30 L).

NMP (330 kg) was charged to the combined mother liquors/wash and the temperature was adjusted to 30±5° C. Methyl iodide (83 kg, 585 mol) was charged and the reactor closed. The temperature was adjusted to 55±5° C. and the reaction mixture was left to react for at least 120 minutes before NMR analysis (solvent: $D_2O$) showed 6% of the residual hydroxy ethanoic acid intermediate.

Sodium sulfite (56 kg, 446 mol) dissolved in water (147 kg) was charged and the mixture was agitated for 30 minutes. The solution was extracted four times for 10 minutes at 30±10° C. using 406 kg toluene in each extraction. The combined organic phase was concentrated by stripping off solvent, under reduced pressure and a maximum temperature of 70° C., until a residual volume of approximately 350 L was reached. The solution was cooled to below 30° C. and transferred to steel barrels over a Millipore filter to give (R)-methyl 2-((S)-2,2-dimethyl-1,3-dioxolan-4-yl)-2-hydroxyacetate solution in toluene (359 kg, 9.4%, 177 mol). Yield: 65%.

$^1$H NMR consistent with commercially available sample of the sub-title product.

iii) (R)-Methyl 2-((S)-2,2-dimethyl-1,3-dioxolan-4-yl)-2-(tosyloxy)acetate

From (R)-Methyl 2-((S)-2,2-dimethyl-1,3-dioxolan-4-yl)-2-hydroxyacetate solution in toluene (359 kg, 9.4%, 177 mol), toluene was distilled off under reduced pressure and a maximum temperature of 70° C. until condensation ceased.

Acetonitrile (153 kg) was charged and the temperature was adjusted to 25±5° C. Triethylamine (41 kg, 405 mol), 4-(dimethyl amino)pyridine (1.12 kg, 9.2 mol) and then, over about 30 minutes, a solution of p-toluenesulfonyl chloride (52.5 kg, 276 mol) in acetonitrile (146 kg) were added at 25±5° C. After stirring the reaction mixture for an additional three hours, NMR analysis (solvent: $d_6$-DMSO) showed acceptable conversion (94%).

MTBE (235 kg) and water (326 kg) were charged and the two-phase system was agitated for about 3 hours, after which time HPLC analysis showed the level of p-toluenesulfonyl chloride to be <0.1% of total peak area. The temperature was adjusted to 25±5° C. and then allowed to separate for 15 minutes. The aqueous phase was taken and extracted with further MTBE (156 kg) before discarding. The 2 organic phases were pooled together and washed with water (326 kg). Then the organic phase was washed 4 times with sodium chloride (16 kg each portion) solution in water (140 kg each portion), each for 5-10 minutes at 25±5° C. Then the organic phase was washed twice with water (185 kg per portion) each for 5-10 minutes at 25±5° C. NMR analysis (solvent: d$_6$-DMSO) then showed <2% NMP (residual from the starting solution), by moles relative to the sulfonate ester intermediate.

Activated carbon (6.0 kg) was charged and the slurry was agitated for 15 minutes at 25±5° C. before the carbon was filtered off in two parallel bag filter. A cartridge filter of 0.6 µm was used after the bag filters. The filters and pipes were rinsed with MTBE (27 kg).

The mother liquors and rinse were combined and reduced in volume by stripping off solvent, under reduced pressure and a maximum temperature of 50° C., until condensation ceased. Heptanes (106 kg) was charged and the solution was reduced once again by stripping off solvent, under reduced pressure and a maximum temperature of 50° C., until condensation ceased, leaving about 60 L solution in the reactor. MTBE (185 kg) was charged followed, after adjusting the temperature to 25±5° C., by heptanes (75 kg). The solution was cooled to 0-5° C. over no less than 30 minutes and heptanes (150 kg) was added over an additional 20 minutes. The slurry was agitated for one hour at 0-5° C. and then filtered. The filter cake was washed with a mixture of MTBE (16 kg) and heptanes (30 kg). The wet product was charged to a vacuum tray dryer and dried at 35° C. (at less than 100 mbar), to give (R)-methyl 2-((S)-2,2-dimethyl-1,3-dioxolan-4-yl)-2-(tosyloxy)acetate (51.3 kg, 154 mol) as a light brown powder. Yield: 87%.

$^1$H NMR (400 MHz, CDCL$_3$) δ 7.83 (m, 2H), 7.35 (m, 2H), 4.84 (d, J=4.8 Hz, 1H), 4.46 (m, 1H), 4.04 (dd, J=6.6, 9.1 Hz, 1H), 3.97 (dd, J=5.2, 9.1 Hz, 1H), 3.70 (s, 3H), 2.45 (s, 3H), 1.30 (s, 3H), 1.29 (s, 3H).

iv) (S)-2,2-Dimethyl-4-((R)-oxiran-2-yl)-1,3-dioxolane (R)-Methyl 2-((S)-2,2-dimethyl-1,3-dioxolan-4-yl)-2-(tosyloxy)acetate (76.1 kg, 221 mol) was dissolved in methanol (57 kg) and dichloromethane (208 kg).

Methanol (14 kg), dichloromethane (53 kg) and one-third of the starting material solution (74 mol) were charged to the reactor. The solution was tempered to 10-15° C. Then, sodium borohydride (6.3 kg, 169 mol) was charged in 18 portions to the reactor holding the temperature 8-15° C. The mixture was stirred for half an hour after complete addition. The next one-third of the starting material solution (74 mol), and more sodium borohydride (6.3 kg, 169 mol) were charged, followed by a half-hour stir, using the same procedure as before. This procedure was again repeated with the final one-third of the starting material solution (74 mol) and more sodium borohydride (6.3 kg, 169 mol). HPLC analysis then showed >99.9% conversion to the intermediate (S)-1-((S)-2,2-dimethyl-1,3-dioxolan-4-yl)-2-hydroxyethyl 4-methylbenzenesulfonate.

Dichloromethane (200 kg) was charged to the reaction mixture. Sodium methoxide solution in methanol (43 kg, 30%, 239 mol) was dosed at 20-25° C. for 60 minutes. After approximately half an hour, HPLC analysis showed 99.7% consumption of the intermediate alcohol.

A solution of sodium acetate (25 kg) in water (230 L) was charged to the reaction mixture. The mixture was stirred for 10-15 minutes at 20-25° C. After separation for 15 minutes the lower organic phase was removed. The upper aqueous phase was extracted with dichloromethane (376 kg). The lower organic phase was removed, combining with the first organic phase, and the aqueous phase was discarded.

Water (359 L) was charged to the combined organic phases. After stirring for 10-15 minutes at 20-25° C. and settling for 15 minutes, the lower organic phase was transferred to a reactor containing sodium sulphate (63 kg).

The volume of the mixture was reduced to 310 L by stripping off solvent, and then the sodium sulphate was filtered off. The filter cake was washed with dichloromethane (94 kg). The combined liquors were thoroughly mixed and then discharged to steel drums via a polypropylene bag filter to give (S)-2,2-dimethyl-4-((R)-oxiran-2-yl)-1,3-dioxolane solution in DCM (467.5 kg, 6.2%, 203 mol) as a clear yellow liquid. Yield: 91%.

A sample, free from solvents, may be isolated on a small scale by evaporation of solvent and then distilling under vacuum.

$^1$H NMR (isolated sample, 400 MHz, d$_6$-DMSO) δ 4.01 (dd, J=6.6, 8.2 Hz, 1H), 3.92 (m, 1H), 3.72 (dd, J=5.8, 8.2 Hz, 1H), 3.03 (ddd, J=2.6, 4.1, 5.2 Hz, 1H), 2.77 (dd, J=4.1, 5.0 Hz, 1H), 2.58 (dd, J=2.6, 5.0 Hz, 1H), 1.34 (s, 3H), 1.27 (s, 3H).

v) (R)-1-((S)-2,2-Dimethyl-1,3-dioxolan-4-yl)ethanol

From (S)-2,2-Dimethyl-4-((R)-oxiran-2-yl)-1,3-dioxolane solution in dichloromethane (465 kg, 6.2%, 200 mol), dichloromethane was distilled at 41-42° C. and replaced by THF (129 kg). Distillation was continued at 60° C. until a set volume in the reactor was reached (235 L). Lithium aluminium hydride (LAH) solution in THF (26.4 kg, 10%, 70 mol) was dosed to the reactor at 22° C. and after subsequent stirring at 25° C. for approximately one hour, GC analysis showed >99.9% consumption of the starting material.

Small portions of water were added via a charging funnel at a rate which was adjusted to control temperature and foaming. A total of 2.6 liters of water (1 L per kg LAH) was added. Sodium hydroxide solution (2.6 kg, 15%, 1 L per kg LAH) was added in the same manner as described for water. Water (7.9 L, 3 L per kg LAH) was charged once more via the charging funnel using the same procedure as before.

The slurry was filtered and the filter cake was washed with THF (36 kg). The filtrate was concentrated by stripping off THF, at a maximum temperature of 85° C., until condensation ceased. 2-MeTHF (129 kg) was charged to the reactor, and then solvent was distilled off to reach a solution volume of approximately 120 L. KF analysis showed <0.1% water. The solution was discharged via a cartridge filter to a PE-lined drum to give (R)-1-((S)-2,2-dimethyl-1,3-dioxolan-4-yl)ethanol solution (103 kg, 27%, 187 mol) as a clear, light yellow liquid. Yield: 94%.

A sample, free from solvents, may be isolated on a small scale by evaporation of solvent and then distilling under vacuum.

$^1$H NMR (isolated sample, 400 MHz, d$_6$-DMSO) δ ppm 4.77 (d, J=5.1 Hz, 1H), 3.95 (dd, J=8.0, 6.2 Hz, 1H), 3.76 (dd, 8.0, 6.0 Hz, 1H), 3.70 (m, 1H), 3.46 (m, 1H), 1.29 (s, 3H), 1.25 (s, 3H), 1.07 (d, J 6.2 Hz, 3H).

Alternatively Intermediate A [(R)-1-[(S)-2,2-dimethyl-1,3-dioxolan-4-yl]ethanol] may be prepares as follows:

Method A:

40 g (1R)-1-[(4S)-2,2-dimethyl-1,3-dioxolan-4-yl]ethyl] 3,4,5 trimethoxybenzoate (117.5 mmol) was dissolved in 7 rel vol (280 mL) methanol. To this solution was charged 20 g 47% w/w aqueous sodium hydroxide (2 equivalents, 235 mmol) and the solution was heated to 50° C. The reaction went to completion typically within 1-2 hrs and was evaporated under reduced pressure. 2-Methyl-tetrahydrofurane (160 mL, 4 rel. vol) was charged and the mixture was evaporated again under reduced pressure to remove traces of methanol. Further 2-methyl-tetrahydrofurane (200 mL, 5 rel.

vol) was charged and the resulting suspension was stirred at ambient temperature for 30 minutes before filtration. The filter cake was washed with 72 mL (1.8 vol) 2-methyl tetrahydrofurane. The clear filtrate was concentrated again under reduced pressure to give the alcohol as colourless oil. Yield: 13.4 g (78%)

Method B:

20 g (1R)-1-[(4S)-2,2-dimethyl-1,3-dioxolan-4-yl]ethyl]-3,4,5-trimethoxybenzoate (58.76 mmol) was dissolved in 10 rel vol (200 mL) 2-methyl tetrahydrofurane. To the clear solution was charged 4.24 mL methyl-tributylammonium chloride (75% aqueous solution, 11.75 mmol) followed by 9.89 g (58.76 mmol) of a 50% aqueous potassium hydroxide solution. The resulting mixture was agitated at 50° C. and went to completion (<1% residual starting material) typically within 20 hrs. The suspension was filtered and the clear filtrate was further dried by distillation under vacuum to approximately 100 mL volume. The mixture was filtered, topped-up with 100 mL 2-methyl tetrahydrofurane and concentrated again to 20 mL total volume. The resulting clear solution was diluted with 30 mL 2-methyl tetrahydrofurane that was previously used to rinse the vessel.

Yield: 50 mL solution in 2-methyl tetrahydrofurane containing 7.9 g (92% th) (R)-1-[(S)-2,2-dimethyl-1,3-dioxolan-4-yl]ethanol A sample, free from solvents, may be isolated on a small scale by evaporation of solvent and then distilling under vacuum.

$^1$H NMR (isolated sample, 400 MHz, d$_6$-DMSO) δ ppm 4.77 (d, J=5.1 Hz, 1H), 3.95 (dd, J=8.0, 6.2 Hz, 1H), 3.76 (dd, 8.0, 6.0 Hz, 1H), 3.70 (m, 1H), 3.46 (m, 1H), 1.29 (s, 3H), 1.25 (s, 3H), 1.07 (d, J=6.2 Hz, 3H).

(1R)-1-[(4S)-2,2-dimethyl-1,3-dioxolan-4-yl]ethyl]-3,4,5-trimethoxybenzoate was prepared as follows:

[(1R,2S)-2,3,-dihydroxy-1-methyl-propyl]3,4,5-trimethoxybenzoate

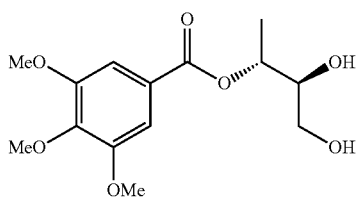 [SMILES: COc1cc(C(=O)O[C@H](C)[C@@H](O)CO)cc(OC)c1OC]

As the yield and enantiomeric excess of the product much depends on the level of residual water in solvents and reagents, the reaction requires the assistance of a drying agent, typically molecular sieves 3 Ångstrom. The combined water content in solvents and reagents should not exceed 0.038 molar equivalents wrt E-crotyl alcohol.

E-crotyl alcohol (20 kg@100% w/w, 277 mol) at approximately 20° C. was passed through a cartridge containing 3 Ångstrom molecular sieve pellets (8 kg) at a constant rate over approximately 80 minutes into a dry collecting vessel. After a hold of approximately 32 minutes the cartridge was blown clear using pressurized nitrogen over approximately 31 minutes. Approximately 85% of the input E-crotyl alcohol was recovered as dried E-crotyl alcohol.

A solution of dried E-crotyl alcohol (20 kg @100% w/w, 277 mol), L-(+)-diisopropyl tartrate (11.7 kg, 50 mol) and toluene (167 kg) at approximately −8° C. was charged with titanium isopropoxide (11.8 kg, 42 mol) and toluene (33 kg).

The batch was agitated for approximately 30 minutes, before charging cumene hydroperoxide (87% w/w, 58.2 kg, 333 mol) and toluene (78 kg) over at least 4 hours. The batch was agitated for approximately 2 hours, before charging 3,4,5-trimethoxybenzoic acid (2.9 kg, 13.9 mol). The batch was then charged over approximately 1 hour to a slurry of titanium isopropoxide (7.9 kg, 28 mol), 3,4,5-trimethoxybenzoic acid (47.1 kg, 222 mol) and toluene (152 kg) at approximately 30° C., followed by a line wash with toluene (17 kg). Titanium isopropoxide (23.7 kg, 83 mol) and toluene (40 kg) were then charged over approximately 2 hours, and the batch was then agitated for approximately 3 hours. The batch was cooled, and then charged with trimethylphosphite (17.2 kg, 139 mol) and toluene (35 kg). The batch was then warmed to approximately 30° C., before washing twice with aqueous hydrochloric acid (10% w/w, 84 kg then 63 kg), and then three times with water (3×60 kg). The combined aqueous phases were then washed with 2-methyltetrahydrofuran (344 kg). The organic phases were combined and then washed with water (60 kg), before distilling under vacuum to a batch volume of approximately 260±40 L.

The temperature was adjusted to approximately 35° C. before hexanes (65 kg) were charged over at least 30 minutes. The batch was then seeded, and then agitated for at least 1 hour before cooling to approximately 0° C. over at least 3 hours. [Seeds may be obtained by removing a portion of the solution to a separate vessel and cooling this to or below the temperature of supersaturation. The precipitating solids can be filtered and returned directly to the main batch to function as seed crystals in a then controlled crystallisation.]

Additional hexanes (325 kg) were charged over at least 2 hours and the slurry was aged for at least a further 1 hour before the solid was isolated by filtration. The solid was washed with hexanes (2×130 kg) and then dried to constant weight. Yield: 57% at 100% w/w. Strength=93% w/w [also contains 3,4,5-trimethoxybenzoic acid (TMBA)].

$^1$H NMR [500 MHz, CDCl$_3$, with 2,3,5,6-tetrachloronitrobenzene (TCNB) as internal standard]; δ 7.71 (s, TCNB), 7.33 (s, residual TMBA), 7.26 (s, 2H), 7.24 (s, CDCl$_3$), 5.13 (m, 1H), 3.89 (m, 9H), 3.73 (m, 2H), 3.63 (1H, m), 1.44 (d, J=6.6 Hz, 2H).

Enantiomeric excess: typically 97%

(1R)-1-[(4S)-2,2-dimethyl-1,3-dioxolan-4-yl]ethyl-3,4,5 trimethoxybenzoate

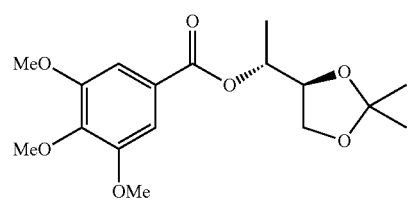 [SMILES: COc1cc(C(=O)O[C@H](C)[C@@H]2COC(C)(C)O2)cc(OC)c1OC]

A solution of [(1R,2S)-2,3,-dihydroxy-1-methyl-propyl]3,4,5-trimethoxybenzoate (43.8 kg @100% w/w, 146 mol, approximately 97% enantiomeric excess) in 2-methyltetrahydrofuran (226 kg) at approximately 30° C. was charged with para-toluenesulfonic acid (0.6 kg, 3 mol). 2,2-Dimethoxypropane (38.0 kg, 365 mol) was then charged over approximately 40 minutes. The batch was agitated for approximately 2.5 hours before charging aqueous potassium bicarbonate solution (7% w/w, 167 kg). The temperature was adjusted to approximately 60° C., before filtering the batch into a static vessel, to remove residual titanium species. The lower, aqueous, phase was removed and the batch was then washed with water (131 kg), before distilling under vacuum to a volume of approximately 130±20 L. Isooctane (212 kg) was charged, and the solution was further distilled under vacuum to volume of approximately 240±20 L. The batch was seeded at 60° C. and then agitated for at least 1 hour before cooling to approximately 5° C. over at least 8 hours. [Seeds may be obtained by removing a portion of the solution to a separate vessel and cooling this to or below the temperature of supersaturation. The precipitating solids can be filtered and returned directly to the main batch to function as seed crystals in a then controlled crystallisation.] The batch was aged for at least 2 hours before the solid was isolated by filtration. The solid was washed with hexanes (85 kg) at approximately −5° C., and then dried to constant weight. Yield: 84% at 100% w/w. Strength=100% w/w.

$^1$H NMR [400 MHz, CDCl$_3$, with 2,3,5,6-tetrachloronitrobenzene (TCNB)]; δ 7.71 (s, TCNB), 7.28 (s, 2H), 7.24 (s, CDCl$_3$), 5.15 (m, 1H), 4.20 (m, 1H), 4.10 (m, 1H), 3.92 (m, 1H), 3.88 (s, 9H), 1.36 (m, 9H).

Enantiomeric excess: typically >99% ee (The isolation temperature may be adjusted, depending on the enantioexcess of the starting [(1R,2S)-2,3,-dihydroxy-1-methyl-propyl]3,4,5-trimethoxybenzoate, and the desired enantioexcess of the isolated (1R)-1-[(4S)-2,2-dimethyl-1,3-dioxolan-4-yl]ethyl-3,4,5 trimethoxybenzoate.)

Intermediate B

3-Methylazetidine-1-sulfonamide

i) Benzyl 3-methylazetidin-1-ylsulfonylcarbamate

Isopropyl acetate (300 mL) was charged into a 1000 ml 3-neck flask and cooled to −10~−5° C. Sulfurisocyanatidic chloride (44.5 mL) was added at −5~10° C. followed by the addition of phenylmethanol (50.5 mL) in isopropyl acetate (60 mL) at −5~10° C. over 60 minutes. The mixture reacted at −5~10° C. and was monitored by HPLC until the content of benzyl alcohol was <2% (after 1 hour at 0 C). A mixture of acetonitrile (300 mL), 3-methylazetidine hydrochloride (50 g) (Intermediate C, either commercially available or prepared as set out below) and triethylamine (162 mL) was stirred in a 2000 mL 3-neck flask and to this was added the solution of the intermediate benzyl chlorosulfonylcarbamate in isopropyl acetate (360 mL) dropwise at <−5° C. over 90 minutes. The mixture was allowed to warm to RT overnight. The reaction was quenched with acetic acid and pH was adjusted to 4~5. The mixture was separated and the aqueous phase was washed with isopropyl acetate (500 ml) and then separated. The organic phase was combined and washed with 10% brine (2×120 ml), dried with anhydrous magnesium sulphate, filtered and the filter cake washed with isopropyl acetate (30 ml) and filtered to afford the sub-title product (145 g) as a red oil.

$^1$H NMR (500 MHz, CDCl$_3$) δ 11.43 (s, 1H), 7.57 (m, 5H), 5.18 (s, 2H), 4.08-3.96 (m, 2H), 3.60-3.50 (m, 2H), 2.67-2.54 (m, 1H), 1.22-1.11 (d, 3H).

ii) 3-Methylazetidine-1-sulfonamide

The sub-title product of step (i) (132 g) split into 2 reactors was added to a stirred solution of 10% Pd/C (4.94 g) in ethanol (1000 mL). The mixture was hydrogenated at 3.00 bar for 16 hours. The solvent was evaporated to afford crude product. The crude product was purified by flash silica chromatography, elution 30% ethyl acetate in dichloromethane (stained with KMnO4). Pure fractions were evaporated to dryness to afford the title product (60.3 g) as a white solid.

$^1$H NMR (500 MHz, CDCl$_3$) δ 6.82 (s, 2H), 3.75 (t, J=8.0 Hz, 2H), 3.36-3.24 (m, 2H), 2.59-2.46 (m, 1H), 1.13 (d, J=6.8 Hz, 3H).

Intermediate C

3-Methylazetidine hydrochloride

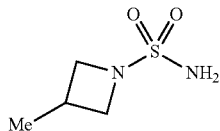

i) Benzyl 3-hydroxyazetidine-1-carboxylate

A solution of azetidin-3-ol (14.7 g) dissolved in THF (170 mL) and water (85 mL) was treated with potassium carbonate (37.1 g) under nitrogen. The mixture was stirred at RT for 30 minutes before cooling to 0° C. and adding benzyl carbonochloridate (20.0 mL) dropwise over 30 minutes at 0° C. The resulting mixture was stirred at 20° C. for 60 hours. The reaction mixture was diluted with water (150 mL), and extracted with ethyl acetate (200 mL). The organic was dried over magnesium sulfate, filtered and evaporated to afford crude product as a colourless oil. The crude product was purified by flash silica chromatography, elution 50% ethyl acetate in isohexane to 100% ethyl acetate. Pure fractions were evaporated to dryness to afford the sub-title product (19.40 g, 69.8%) as a colorless oil.

$^1$H NMR (500 MHz, CDCL$_3$) δ 7.41-7.28 (m, 5H), 5.09 (s, 2H), 4.70-4.54 (m, 1H), 4.23 (dd, J=6.7, 9.9 Hz, 2H), 3.89 (dd, J=4.4, 10.0 Hz, 2H), 2.34 (d, J=6.1 Hz, 1H).

ii) Benzyl 3-oxoazetidine-1-carboxylate

A solution of the sub-title product of step (i) (17.9 g) in DMSO (100 mL) was added dropwise over 15 minutes to a solution of pyridine sulphur trioxide (44.7 g) and triethylamine (39.3 mL) in DMSO (200 ml) at 0° C. (slight exotherm to 5 C). The mixture was warmed to RT after 5 minutes and stirred for 16 hours. The mixture was poured into ice/water and extracted twice with ethyl acetate. The combined organics were washed with brine, dried over sodium sulfate and concentrated in vacuo to give crude product. The crude product was purified by flash silica chromatography, elution 100% dichloromethane. Pure fractions were evaporated to dryness to afford the sub-title product (17.9 g) as a pale yellow oil.

¹H NMR (500 MHz, CDCL₃) δ 7.40-7.31 (m, 5H), 5.17 (s, 2H), 4.78 (s, 4H).

iii) Benzyl 3-methyleneazetidine-1-carboxylate

A suspension of methyltriphenylphosphonium bromide (93 g) and potassium tert-butoxide (29.3 g) in diethyl ether (700 mL) was stirred at RT for 20 minutes and heated at 35° C. for 1 hour under nitrogen. The bright yellow mixture was treated with the sub-title product of step (ii) (17.9 g) in diethyl ether (200 mL) dropwise over 1 hour at 35° C. (orange suspension formed). The resulting mixture was stirred at 35° C. for 12 hours. The mixture was cooled and filtered through a pad of celite and washed with diethyl ether. The filtrate was washed with water (300 mL), dried over magnesium sulfate, filtered and evaporated to afford crude product. The crude product was purified by flash silica chromatography, elution 10% ethyl acetate in isohexane to 50% ethyl acetate in isohexane (stained with KMnO4). Pure fractions were evaporated to dryness to afford the sub-title product (14.1) as a colorless oil.

¹H NMR (400 MHz, CDCL₃) δ 7.39-7.28 (m, 5H), 5.12 (s, 2H), 5.01 (m, 2H), 4.57 (t, 4H).

iv) 3-Methylazetidine hydrochloride

A solution of the sub-title product of step (iii) (14.1 g) dissolved in ethanol (100 mL) was treated with 10% Pd/C (JM type 87L) (1.48 g) under hydrogen. The resulting mixture was stirred at 20° C. for 40 hours at 4.50 bar pressure of hydrogen gas. The Cbz protecting group still attached so switched to palladium hydroxide on carbon (2 g) in ethanol (100 mL). The mixture was hydrogenated for a further 24 hours at 4.50 bar. The mixture was filtered through a pad of celite and filtrate cooled to 0° C. in an ice batch. 4M HCl in dioxane (26.0 mL) was added dropwise and the solution evaporated to dryness to give the title product (7.46 g) as a light brown oil.

¹H NMR (400 MHz, CDCL₃) δ 9.24 (s, 2H), 3.95 (ddd, J=7.4, 9.8, 11.4 Hz, 2H), 3.55-3.45 (m, 2H), 2.85 (dt, J=6.7, 14.2 Hz, 1H), 1.16 (d, 3H).

The invention claimed is:

1. A method of treating a chemokine mediated disease state in a mammal suffering from, or at risk of, said disease, which comprises administering to a mammal in need of such treatment a therapeutically effective amount of (a) a pyrimidine sulfonamide of formula (I), or (b) a pharmaceutically acceptable salt thereof:

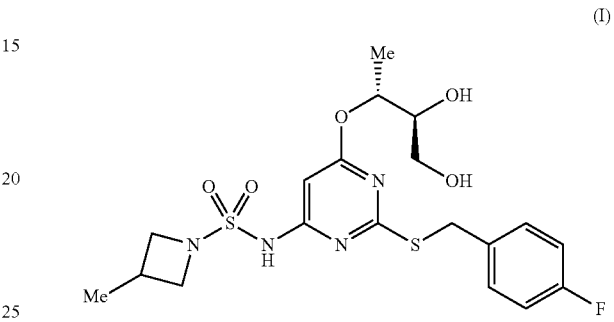

(I)

wherein the chemokine mediated disease state is an inflammatory disease selected from asthma, allergic rhinitis, chronic obstructive pulmonary disease, inflammatory bowel disease, irritable bowel syndrome, osteoarthritis, osteoporosis, rheumatoid arthritis or psoriasis.

2. The method of claim 1, further comprising administering to the mammal a therapeutically effective amount of an anti-gout agent, a xanthine oxidase, and/or a uricosuric agent.

* * * * *